US007195898B2

(12) United States Patent
Ben-Bassat et al.

(10) Patent No.: US 7,195,898 B2
(45) Date of Patent: Mar. 27, 2007

(54) METHOD FOR THE PRODUCTION OF P-HYDROXYBENZOATE IN SPECIES OF PSEUDOMONAS AND AGROBACTERIUM

(75) Inventors: Arie Ben-Bassat, Newark, DE (US); Monica Cattermole, Newark, DE (US); Anthony A. Gatenby, Wilmington, DE (US); Katharine J. Gibson, Wilmington, DE (US); M. Isabel Ramos-Gonzalez, Granada (ES); Juan Ramos, Granada (ES); Sima Sariaslani, Newark, DE (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/484,129

(22) Filed: Jul. 11, 2006

(65) Prior Publication Data
US 2006/0246559 A1 Nov. 2, 2006

Related U.S. Application Data

(62) Division of application No. 10/464,952, filed on Jun. 19, 2003, now Pat. No. 7,083,953.

(51) Int. Cl.
C12P 17/14 (2006.01)
C12P 7/00 (2006.01)
C12N 15/00 (2006.01)
C12N 9/00 (2006.01)

(52) U.S. Cl. .................. 435/120; 435/132; 435/320.1; 435/252.34; 435/69.1; 435/195; 435/183

(58) Field of Classification Search ................ 435/120, 435/132, 320.1, 252.34, 69.1, 195, 183
See application file for complete search history.

(56) References Cited

U.S. PATENT DOCUMENTS

| 3,985,797 | A | 10/1976 | Massie ................ 260/502.4 R |
| 4,657,863 | A | 4/1987 | Maxwell ..................... 435/142 |
| 4,740,614 | A | 4/1988 | Fjare .......................... 562/416 |
| 4,910,143 | A | 3/1990 | Vandenbergh ......... 435/252.34 |
| 4,968,612 | A | 11/1990 | Hsieh .......................... 435/142 |
| 5,017,495 | A | 5/1991 | Yen .......................... 435/320.1 |
| 5,079,166 | A | 1/1992 | Winter ........................ 435/262 |
| 5,399,178 | A | 3/1995 | Cherpeck ..................... 44/415 |
| 5,543,317 | A | 8/1996 | Shields et al. ............ 435/240.2 |
| 2003/0207322 | A1 | 11/2003 | Ben-Bassat et al. |

FOREIGN PATENT DOCUMENTS

| EP | 1108790 | 6/2001 |
| WO | WO 92/06208 | 4/1992 |
| WO | WO 98/56920 | 12/1998 |
| WO | WO 0009682 | 2/2000 |

OTHER PUBLICATIONS

Byrne et al., "Cascade Regulation of The Toluene-3-Monooxygenase Operon (tbuA1UBVA2C) of Burkholderia pickettii PK01: Role of the tbuA1 Promoter (PtbuA1) in the Expression of its Cognate Activator, TbuT," Journal of Bacteriology 178 (21): 6327-6337 (1996).
Cronin et al., "Organization and Sequences of p-Hydroxybenzaldehyde Dehydrogenase and Other Plasma-encoded Genes for Early Enzymes of the p-Cresol Degradative Pathway in Pseudomona putida NCIMB 9866 and 9869," DNA Sequence 1 (10): 7-17 (1999).
Hewetson et al., "Evidence for a Transmissible Catabolic Plasmid in Pseudomona putida Encoding the Degradation of p-Cresol via the Protocatechuate ortho Cleavage Pathway," Genet. Res., Camb. 3 (32): 249-255 (1978).
Kim et al., "Cloning, sequencing and expression of the structural genes for the cytochrome and flavoprotein subunits of p-cresol methylhydroxylase from two strains of Pseudomonas putida," Journal of Bacteriology 176 (20): 6349-6361 (1994).
Mosqueda, et al., "Toluene metabolism by the solvent-tolerant Pseudomonas putida DOT-T1 strain, and its role in solvent impermeabilization," Gene, 232 (1): 69-76 (1999).
International Search Report, PCT/US 01/16574, mailed Sep. 11, 2002.
Byrne et al., J. Bacteriol., 176 3749-3756 (1996).
Kwang-Mu Yen, et al. Cloning and Characterization of a Pseudomonas mendocina KR1 Gene Cluster Encoding Toluene-4-Monooxygenase, Journal of Bacteriology, vol. 173, No. 17 (Sep. 1991), pp. 5315-5327.
Armando M. Byrne, et al., Cascade Regulation of the Toluene-3-Monooxygenase Operon (tbuA1UBVA2C) of Burkholderia picketti PK01: Role of the tbuA1 Promoter (PtbuA1) in the Expression of Its Cognate Activator, TbuT, Journal of Bacteriology, vol. 178, No. 1996 (Nov. 1996), pp. 6327-6337.
Andrzej Kalinski, et al. Molecular Cloning of a Protein Associated with Soybean Seed Oil Bodies That is Similar to Thiol Proteases of the Papain Family, The Journal of Biological Chemistry, vol. 265, No. 23 (Aug. 1990), pp. 13843-13848.
Whited, Gregory M. et al., Separation and Partial Characterization of the Enzymes of the Toluene-R-Monooxygenase Catabolic Pathway in Pseudomonas mendocina KR1, Journal of Bacteriology, 173, No. 9, 3017-3020, May 1991.
Johnson, Glenn R. et al., Multiple Pathways for Toluene Degradation in Burkholderia sp. Strain JS150, Applied and Environmental Microbiology, 63, No. 10, 4047-4052, Oct. 1997.

(Continued)

Primary Examiner—Maryam Monshipouri
(74) Attorney, Agent, or Firm—Myers, Bigel, Sibley & Sajovec, P.A.

(57) ABSTRACT

Bacterial strains transformed with the pcu genes are useful for the production of para-hydroxybenzoate (PHBA). Applicant has provided the p-cresol utilizing (pcu) and tmoX gene sequences from Pseudomonas mendocina KR-1, the proteins encoded by these sequences, recombinant plasmids containing such sequences, and bacterial host cells containing such plasmids or integrated sequences. Method for the use of these materials to produce PHBA are also disclosed.

7 Claims, 4 Drawing Sheets

OTHER PUBLICATIONS

Tay, Stephen T.-L. et al., Two New *Mycobacterium* Strains and their Role in Toluene Degradation in a Contaminated Stream, *Applied and Environmental Microbiology*, 64, No. 5, 1715-1720, May 1998.

Zylstra, G. J. et al., Aromatic Hydrocarbon Degradation by Sphingomonas Yanoikuyae B1, *Journal of Industrial Microbiology & Biotechnology*, 19, 408-414, 1997.

Kosono, Saori et al., Three of the Seven BPHC Genes of *Rhodococcus erythropolis* TA421, Isolated from a Termite Ecosystem, are Located on an Indigenous Plasmid Associated with Biphenyl Degradation, *Applied and Environmental Microbiology*, 63, No. 8, 3282-3285, Aug. 1997.

Romine, M. F. et al., Improving the Biodegradative Capacity of Subsurface Bacteria, *Bioremediation of Chlorinated and Polycyclic Aromatic Hydrocarbon Compounds*, 271-276, 1994.

Frazee, Richard W., et al., Cloning, Sequencing, and Expression of the *Pseudomonas putida* Protocatechuate 3,4-Dioxygenase Genes, *Journal of Bacteriology*, 175, No. 19, 6194-6202, Oct. 1993.

Romero-Steiner, Sandra, et al., Characterization of the PCAR Regulatory Gene from *Pseudomonas putida*, Which is Required for the Complete Degradation of P-Hydroxybenoate, *Journal of Bacteriology*, 176, No. 18, 5771-5779, Sep. 1994.

Dimarco, Anthony A., et al., Regulation of P-Hydroxybenzoate Hydroxylase Synthesis by PQBR Bound to an Operator in *Acinetobacter calcoaceticus*, *Journal of Bacteriology*, 176, No. 14, 4277-4284, Jul. 1994.

Wong, Cheryl M., et al., Cloning and Sequencing Show that 4-Hydroxybenzoate Hydroxylase (POBA) is Required for Uptake of 4-Hydroxybenzoate in *Rhizobium leguminosarum*, *Microbiology*, 2775-2786, 1994.

Entsch, Barrie, et al., Sequence and Organization of POBA, the Gene Coding for P-Hydroxybenzoate Hydroxylase, an Inducible Enzyme from *Pseudomonas aeruginosa*, *Gene*, 279-291, 1988.

Miller, Edward S., et al., Bioconversion of Toluene to P-Hydroxybenzoate via the Construction and Characterization of a Recombinant *Pseudomonas putida*, *Green Chemistry*, 143-152, Jun. 1999.

Wright, Alice, et al., Self-Mobilization and Organization of the Genes encoding the Toluene Metabolic Pathway of *Pseudomonas mendocina* KR1, *Applied and Environmental Mirobiology*, 60, No. 1, 235-242, Jan. 1994.

METHOD FOR THE PRODUCTION OF P-HYDROXYBENZOATE IN SPECIES OF PSEUDOMONAS AND AGROBACTERIUM

RELATED APPLICATIONS

This application is a divisional of and claims priority to U.S. application Ser. No. 10/464,952, filed Jun. 19, 2003, now U.S. Pat. No. 7,083,953, which claims priority to U.S. application Ser. No. 09/585,174, filed Jun. 1, 2000, and issued on Jul. 1, 2003 as U.S. Pat. No. 6,586,229, the entire contents of each of which are incorporated by reference herein.

FIELD OF INVENTION

The present invention relates to the fields of molecular biology and microbiology, and to the use of genetic techniques to introduce a modified pathway for the production of desired compounds. More specifically, this invention describes genetically engineered biocatalysts possessing an enhanced, or new, ability to transform p-cresol or toluene to p-hydroxybenzoate.

BACKGROUND OF THE INVENTION p-Hydroxybenzoate (PHBA) is used as a monomer for synthesizing Liquid Crystal Polymers (LCP). LCP's are used in electronic connectors and in telecommunication and aerospace applications. LCP resistance to sterilizing radiation suits these materials for use in medical devices as well as in chemical, and food packaging applications. Esters of PHBA also are used as backbone modifiers in other condensation polymers (i.e., polyesters), and are also used to make parabens preservatives.

Chemical synthesis of PHBA is known. For example, JP 05009154 teaches a chemical route using the Kolbe-Schmidt process from tar acid and $CO_2$ involving 1) the extraction of tar acid from a tar naphthalene oil by an aqueous potassium hydroxide, 2) adding phenol to the extracted tar acid potassium salt, 3) removing $H_2O$, and 4) reacting the resultant slurry with $CO_2$. Alternative methods of chemical synthesis are known (see, for example, U.S. Pat. Nos. 5,399,178; 4,740,614; and 3,985,797).

However, chemical synthesis of PHBA is problematic and costly due to the high energy needed for synthesis and the extensive purification of product required. An alternate low cost method with simplified purification would represent an advance in the art. Biological production offers one such low cost, simplified solution to this problem.

Microbiological methods of PHBA synthesis are known. For example, JP 06078780 teaches PHBA preparation by culturing benzoic acid in the presence of microorganisms (preferably *Aspergillus*) that oxidize benzoic acid to PHBA.

An alternate method of biological production is suggested by bacteria that have an enzymatic pathway for the degradation of toluene and other organics where PHBA is produced as an intermediate. The first enzyme in the toluene degradation pathway is toluene monooxygenase (TMO) and the pathway is referred to as the TMO pathway. The steps of the TMO pathway have been described (Whited and Gibson, *J. Bacteriol.* 173:3010–3020 (1991)) and are illustrated in FIG. 1. Bacteria that possess the toluene degradation pathway are found in the genus *Pseudomonas* where *Pseudomonas putida, Pseudomonas fluorescens, Pseudomonas aeruginosa* and *Pseudomonas mendocina* are the most commonly utilized species. Other examples of aerobic bacteria that are known to degrade toluene are *Burkholderia* (Johnson et al., *Appl. Environ. Microbiol.* 63:4047–4052 (1997)), *Mycobacterium* (Stephen et al., *Appl. Environ. Microbiol.* 64:1715–1720 (1998)), *Sphingomonas* (Zylstra et al., *J. Ind. Microbiol Biotechnol.* 19:408–414 (1997)) and *Rhodococcus* (Kosono et al., *Appl. Environ. Microbiol.* 63:3282–3285 (1997)). In addition, several different species of anaerobic bacteria are known to utilize toluene (Heider et al., *Anarobe* 3:1–22 (1997)). Toluene degradation pathways have been highly characterized (Romine et al., *In Bioremediation of Chlorinated Polycyclic Aromatic Hydrocarbon Compounds;* Hinchee, R. E., Ed.; Lewis: Boca Raton, Fla., 1994; pp 271–276) and a number of the genes encoding key enzymes have been cloned and sequenced, including the protocatechuate 3,4-dioxygenase genes (Frazee, *J. Bacteriol.* 175 (19):6194–6202 (1993)), the pcaR regulatory gene from *Pseudomonas putida,* which is required for the complete degradation of p-hydroxybenzoate (Romero-Steiner et al., J. Bacteriol. 176(18):5771–5779 (1994); Dimarco et al., *J. Bacteriol.* 176(14):4277–4284 (1994)) and the pobA gene encoding the expression of p-hydroxybenzoate hydroxylase (PHBH), the principal enzyme for the conversion of PHBA to protocatechuate (Wong et al., *Microbiology* (Reading U.K.) 140(10):2775–2786 (1994); Entsch et al., *Gene* 71(2): 279–291 (1988)).

Bacteria that possess the TMO pathway are useful for degrading toluene and trichloroethylene. They are able to use these and other organics as sole carbon sources where they are transformed through PHBA to ring-opening degradation products (U.S. Pat. Nos. 5,017,495; 5,079,166; 4,910,143). By using the chromosomal TMO pathway, in combination with mutations that prevent PHBA degradation in *Pseudomonas mendocina* KR1, it has been shown that PHBA can be accumulated by oxidation of toluene (PCT/US98/12072).

Recently, various strains of *Pseudomonas* possessing the toluene degradation pathways have been used to produce muconic acid via manipulation of growth conditions (U.S. Pat. Nos. 4,657,863; 4,968,612). Additionally, strains of *Enterobacter* with the ability to convert p-cresol to PHBA have been isolated from soil (JP 05328981). Further, JP 05336980 and JP 05336979 disclose isolated strains of *Pseudomonas putida* with the ability to produce PHBA from p-cresol. Additionally, Miller and coworkers (*Green Chem.* 1(3):143–152 (1999)) have shown the bioconversion of toluene to PHBA via the construction of a recombinant *Pseudomonas putida.* Their initial catalyst development focused on *Pseudomonas mendocina* KR1 for production of PHBA from toluene. However, they were unable to obtain significant accumulation of PHBA from toluene using this strain. This result was due to their inability to obtain a sufficient disruption of PobA activity (the enzyme catalyzing m-hydroxylation of PHBA to protocatechuate in the protocatechuate branch of the β-ketoadipate pathway; see FIG. 1).

Although the presence of the TMO pathway in *Pseudomonas mendocina* KR1 has been documented (Wright and Olsen, *Applied Environ. Microbiol.* 60(1):235–242 (1994)), the art has not provided a molecular characterization and sequence of the pcu genes encoding the enzymes that transform p-cresol to PHBA in this organism. The art has also not provided bacterial host cells harboring novel recombinant plasmids encoding the enzymes of p-cresol to PHBA oxidation, together with operably-linked native promoter and regulatory sequences and proteins. Such bacterial host strains, if they lack the enzymes to degrade PHBA further, can accumulate PHBA when cultured in the presence of p-cresol.

As an alternative to culturing cells in the presence of p-cresol, the latter compound can be formed from toluene in cells that additionally harbor plasmid-encoded toluene monooxygenase. A bacterial strain harboring plasmid-encoded tmo and pcu operons has not been fully described in the art, particularly a strain that exceeds the production level of PHBA when compared to plasmid-free *Pseudomonas mendocina* KR1. In addition, expression of the tmo operon using its native toluene-induced promoter localized upstream of a tmoX gene previously has not been known. Therefore, the problem to be solved is the lack of a fully characterized pcu operon and the availability of a bacterial strain harboring plasmid-encoded tmo and pcu operons to use for the bioproduction of PHBA.

SUMMARY OF THE INVENTION

The present invention solves the problem of extensively characterizing the pcu operon by providing cloned, sequenced, and expressed genes of the pcu operon from *Pseudomonas mendocina* KR-1 that can be transformed into and used to produce PHBA from p-cresol in *Pseudomonas putida* and *Agrobacterium rhizogenes* strains that do not normally possess this capability. In addition, transformation of the pcu operon into *Pseudomonas mendocina* KRC16KDpobA51 supplements the endogenous pcu operon leading to an increase in PHBA production. This increase in PHBA production in *Pseudomonas mendocina* KRC16KDpobA51 transformed with plasmid-encoded pcu is an improvement over PCT/US98/12072

The present invention provides a method for the production of PHBA comprising: (i) culturing a *Pseudomonas, Agrobacterium* or related strain transformed with a pcu operon in a medium containing an aromatic organic substrate, at least one suitable-fermentable carbon source, and a nitrogen source, wherein the supplied pcu operon comprises genes encoding the TMO toluene degradation pathway enzymes p-cresol methylhydroxylase and p-hydroxy-benzaldehyde dehydrogenase, the transcriptional activator PcuR, wherein the transformed *Pseudomonas* or *Agrobacterium* strain does not produce any detectable p-hydroxybenzoate hydroxylase, whereby PHBA accumulates; and (ii) recovering the PHBA.

The present invention also encompasses the combination of the pcu and tmo operons on a single replicon such that expression of tmo is obtained by transcription from a previously undisclosed toluene or p-cresol induced tmoX promoter, and expression of pcu is obtained by transcription using a previously undisclosed sequence encoding a transcriptional activator.

Another preferred embodiment of the present invention includes the recombinant plasmid pMC4 in *Pseudomonas putida* DOT-T1. This strain synthesized the highest levels of tmo and pcu-encoded enzymes observed and is described herein.

It has also been found that the heterologous todST proteins that control the induction of toluene dioxygenase pathway induce high levels of expression from the tmo pathway genes, and are useful tools to mediate expression of the catabolic tmo genes and PHBA production in any organism that does not possess these genes.

BRIEF DESCRIPTION OF THE DRAWINGS SEQUENCE DESCRIPTIONS, AND BIOLOGICAL DEPOSITS

The invention can be more fully understood with reference to the drawings, from the detailed description, and the sequence descriptions which form part of this application.

Figure 1:
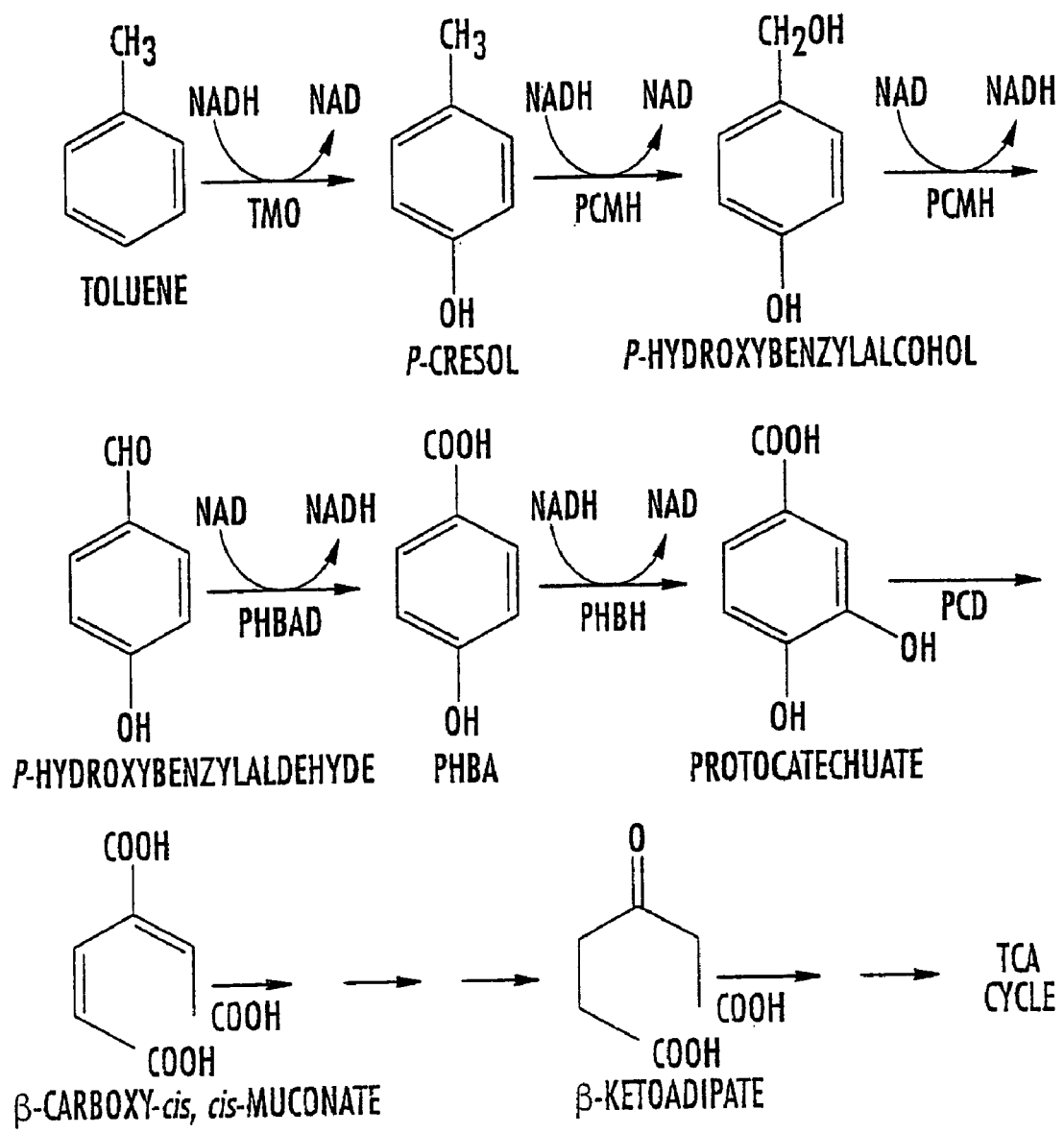
FIG. 1 illustrates the pathway of the toluene degradation in *Pseudomonas mendocina* KR-1.

The following 112 sequence descriptions contained in the sequences listing attached hereto comply with the rules governing nucleotide and/or amino acid sequence disclosures in patent applications as set forth in 37 C.F.R. §1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST2.5 (1998) and the sequence listing requirements of the EPO and PCT (Rules 5.2 and 49.5(a-bis), and-Section-208 and Annex C of the Administration Instructions). The Sequence Descriptions contain the one letter code for nucleotide sequence characters and the three letter codes for amino acids as defined in conformity with the IUPAC-IYUB standards described in *Nucleic Acids Res.* 13:3021–3030 (1985) and in the *Biochemical Journal* 219:345–373 (1984) which are herein incorporated by reference.

SEQ ID NO:1 is the nucleotide sequence of the pcu operon isolated from *Pseudomonas mendocina* KR-1 (6491 bp).

SEQ ID NO:2 is the deduced amino acid sequence of the transcriptional activator PcuR encoded by ORF1.1 (SEQ ID NO:98).

SEQ ID NO:3 is the deduced amino acid sequence of PcuC encoded by ORF1.2 (SEQ ID NO:99) which has the enzyme activity of PHBAD.

SEQ ID NO:4 is the deduced amino acid sequence of PcuA encoded by ORF1.3 (SEQ ID NO:100) which has the enzyme activity of PCMH.

SEQ ID NO:5 is the deduced amino acid sequence of PcuX encoded by ORF1.4 (SEQ ID NO:101) which is an unidentified open reading frame and which may be an inner membrane protein.

SEQ ID NO:6 is the predicted amino acid sequence of PcuB encoded by ORF1.5 (SEQ ID NO:102) which has the enzyme activity of PCMH.

SEQ ID NOs:7–77 are the nucleotide sequences of primers used for sequencing pcu.

SEQ ID NOs:78–79 are the nucleotide sequences of primers used for cloning a *Pseudomonas putida* (NCIMB 9869) pchC gene.

SEQ ID NOs:80–90 are the nucleotide sequences of primers used for sequencing tmoX.

SEQ ID NO:91 is the nucleotide sequence of the tmoX gene and its 5' non-translated region from *Pseudomonas mendocina* KR-1.

SEQ ID NO:92 is the deduced amino acid sequence of TmoX encoded by ORF2.1 (SEQ ID NO:103).

SEQ ID NOs:93–94 are the nucleotide sequences of primers used for cloning pcu for insertion into pMC3.

SEQ ID NOs:95–96 are the nucleotide sequence of primers used for constructing plasmids pPCUR1 and pPCUR2.

SEQ ID NO:97 is the nucleotide sequence of the primer used to map the transcript initiation site of tmoX.

SEQ ID NO:98 is the nucleotide sequence of the transcriptional activator PcuR (ORF1.1).

SEQ ID NO:99 is the nucleotide sequence of PcuC (ORF1.2).

SEQ ID NO:100 is the-nucleotide sequence of PcuA (ORF1.3).

SEQ ID NO:101 is the nucleotide sequence of PcuX (ORF1.4).

SEQ ID NO:102 is the nucleotide sequence of PcuB (ORF1.5).

SEQ ID NO:103 is the nucleotide sequence of the tmoX gene from *Pseudomonas mendocina* KR-1 (ORF2.1).

SEQ ID NO:104 is a primer used to identify the pobA gene.

SEQ ID NO:105 is a primer used to identify the pobA gene.

SEQ ID NO:106 is a primer used to identify the pobA gene.

SEQ ID NO:107 is a primer used to identify the pobA gene.

SEQ ID NO:108 is a primer used to identify the pobA gene.

SEQ ID NO:109 is a primer used to identify the pobA gene.

SEQ ID NO:110 is a primer used to identify the pobA gene.

SEQ ID NO:111 is a primer used to identify the pobB gene.

SEQ ID NO:112 is the nucleotide sequence of the todST genes.

Applicant has made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Pseudomonas mendocina* KRC16KDpobA51 | ATCC 55885 | |

The Depositor has authorized the Applicant to refer to the deposited material in the application and has given his unreserved and irrevocable consent to the deposited material being made available to the public in accordance with Rule 28 of the Implementing Regulations to the European Patent Convention (Rule 28(1)(d) EPC).

DETAILED DESCRIPTION OF THE INVENTION

PHBA is a valuable monomer for the synthesis of liquid crystalline polymers (LCP). Applicants have provided methods for the biological production of PHBA from genetically engineered *Pseudomonas, Agrobacterium,* or related strains transformed with a pcu operon. The instant methods provide PHBA without the high energy cost of synthetic production and without producing toxic waste streams. Applicants have also provided a method for the biological production of p-cresol from genetically engineered *Escherichia* or *Pseudomonas.*

The following abbreviations and definitions will be used to interpret the specification and the claims.

"para-Hydroxybenzoic acid", "para-hydroxybenzoate", "p-hydroxybenzoate" or "4-hydroxybenzoic acid" is abbreviated PHBA.

"para-Hydroxybenzoate hydroxylase" is abbreviated PHBH.

"Toluene-4-monooxygenase" is abbreviated TMO.

"para-Cresol methylhydroxylase" is abbreviated PCMH.

"para-Hydroxybenzaldehyde dehydrogenase" is abbreviated PHBAD.

"Ethylenediaminetetraacetic acid" is abbreviated EDTA.

"Isopropyl-β-D-thiogalactopyranoside" is abbreviated IPTG.

"Shrimp alkaline phosphatase" is abbreviated SAP.

"Calf intestinal alkaline phosphatase" is abbreviated CIP.

"Phenazine ethosulfate" is abbreviated PES.

"2,6-Dichlorophenol-indophenol" is abbreviated DCPIP.

"SSC" is the abbreviation for 150 mM NaCl, 15 mM sodium citrate, pH 7.0.

"TE" is the abbreviation for 10 mM Tris-HCl, 1 mM EDTA, pH 8.0.

The term "amp" refers to ampicillin.
The term "chl" refers to chloramphenicol.
The term "kan" refers to kanamycin.
The term "strep" refers to streptomycin.
The term "Pip" refers to piperacillin.
The term "tet" refers to tetracycline.
The term "strR" refers to a gene conferring resistance to streptomycin.

The terms "TMO degradative pathway" or "TMO enzymatic pathway" refer to the enzymes and genes encoding the enzymes found in some *Pseudomonas bacteria* that are responsible for the degradation of toluene, p-cresol and similar aromatic substrates. The TMO pathway is outlined in FIG. 1 and contains at least toluene-4-monooxygenase (TMO), p-cresol methylhydroxylase (PCMH), p-hydroxybenzoaldehyde dehydrogenase (PHBAD), and p-hydroxybenzoate hydroxylase (PHBH).

The term "aromatic organic substrate" refers to an aromatic compound that is degraded by the TMO enzymatic pathway. Typical examples of suitable aromatic substrates are toluene, p-cresol, p-hydroxybenzyl, and p-hydroxybenzaldehyde.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome-integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitate transformation of a particular host cell.

An "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

"Substantially similar" refers to nucleic acid molecules wherein changes in one or more nucleotide bases result in substitution of one or more amino acids, but do not affect the functional properties of the protein encoded by the DNA sequence. "Substantially similar" also refers to nucleic acid molecules wherein changes in one or more nucleotide bases do not affect the ability of the nucleic acid molecule to mediate alteration of gene expression by antisense or co-suppression technology. "Substantially similar" also refers to modifications of the nucleic acid molecules of the instant invention (such as deletion or insertion of one or more nucleotide bases) that do not substantially affect the functional properties of the resulting transcript vis-à-vis the ability to mediate alteration of gene expression by antisense or co-suppression technology or alteration of the functional properties of the resulting protein molecule. The invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology;* Lesk, A. M., Ed.; Oxford University Press: New York, 1988; *Biocomputing: Informatics and Genome Projects;* Smith, D. W., Ed.; Academic Press: New York, 1993; *Computer Analysis of Sequence Data,* Part I; Griffin, A. M. and Griffin, H. G., Eds.; Humana Press: New Jersey, 1994; *Sequence Analysis in Molecular Biology;* von Heinje, G., Ed.; Academic Press: New York, 1987; and *Sequence Analysis Primer;* Gribskov, M. and Devereux, J., Eds.; Stockton Press: New York, 1991. Preferred methods to determine identity are designed to give the largest match between the sequences tested.

Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci.* USA 85:2444–2448 (1988). The BLASTX program is publicly available from NCBI and other sources (BLAST Manual, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990); Altschul et al., "Gapped BLAST and PSI-BLAST: a new generation of protein database search programs", *Nucleic Acids Res.* 25:3389–3402 (1997)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without affecting the amino acid sequence of an encoded polypeptide. Accordingly, the instant invention relates to any nucleic acid molecule that encodes all or a substantial portion of the amino acid sequence encoding the PcuR, PcuC, PcuA, PcuX and PcuB proteins as set forth in SEQ ID NO:2 through SEQ ID NO:6, and also to any nucleic acid molecule that encodes all or a substantial portion of the amino acid sequence encoding the TmoX protein as set forth in SEQ ID NO:92. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. An "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA molecules of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotech.* 3:225 (1995)).

The "3' non-coding sequences" refer to DNA sequences located downstream of a coding sequence and include recognition sequences and other sequences encoding regulatory signals capable of affecting mRNA processing or gene expression. The use of different 3 non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet and has an effect on cellular processes.

The term "operably linked" refers to the association of nucleic acid sequences on a single nucleic acid molecule so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid molecule of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in organisms in amounts or proportions that are not characteristic of normal, wild-type, or non-transformed organisms. The altered level may be either an increase or decrease in the amount or proportion of gene product relative to that produced by the normal, wild-type, or non-transformed organism.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "fragment" constitutes a fraction of the DNA sequence of the particular region.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign-host.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the transcribed messenger RNA is translated into the above-mentioned gene product if the gene product is a protein.

The terms "restriction endonuclease" and "restriction enzyme" refer to an enzyme which binds and cuts within a specific nucleotide sequence within double-stranded DNA.

"Polymerase Chain Reaction" and "PCR" refer to a method that results in the linear or logarithmic amplification of nucleic acid molecules. PCR generally requires a replication composition consisting of, for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.).

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

The term "carbon source" refers to a substrate suitable for bacterial cell growth that is distinct from the aromatic substrate. Suitable carbon substrates include but are not limited to glucose, succinate, lactate, acetate, ethanol, monosaccharides, oligosaccharides, polysaccharides, or mixtures thereof.

The term "suicide vector" refers to a vector generally containing a foreign DNA fragment to be expressed in a suitable host cell, coupled with a genetic element that will be lethal to the host cell unless the cell is able to express the foreign DNA. "Suicide vector" is also understood to mean a non-replicating vector capable of transfecting a host cell and facilitating the incorporation of foreign DNA into the genome of the host cell. Such a vector does not replicate and is thus destroyed after incorporation of the heterologous DNA. Examples of common suicide vectors and their construction may be found in Sambrook, J., Fritsch, E. F. and Maniatis, T. *Molecular Cloning: A Laboratory Manual;* Cold Spring Harbor Laboratory Press: Cold Spring Harbor, N.Y., 1989.

The meaning of abbreviations is as follows: "h" means hour(s), "min" means minute(s), "sec" means second(s), "d" means day(s), "L" means microliters, "mL" means milliliters and "L" means liters.

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Natl. Acad. Sci.* USA 82, 1074, (1985)) or strand displacement amplification (SDA, Walker, et al., *Proc. Natl. Acad. Sci.* U.S.A., 89, 392, (1992)).

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be used as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. Adv. *Immunol.* 36:1 (1984); Maniatis).

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host for the synthesis of new products heretofore not possible using the host. Additionally the gene products may be useful for conferring higher growth yields of the host or for enabling alternative growth mode to be utilized.

DESCRIPTION OF THE PREFERRED EMBODIMENTS

TMO-Containing Bacterial Strains:

Bacterial cells preferred in the present invention are those that possesses the TMO pathway. Such strains are generally restricted to the genus *Pseudomonas* and include, but are not limited to, *Pseudomonas putida* and *Pseudomonas mendocina*. Strains of *Burkholderia* and *Acinetobacter* are also suitable as host cells.

Strains of *Pseudomonas* containing the TMO pathway are known to oxidize toluene to form intermediates of the tricarboxylic acid cycle. PHBA as well as other intermediates, such as p-cresol, p-hydroxybenzyl alcohol and p-hydroxybenzadehyde, are formed in the upper pathway, which metabolizes toluene to the ring cleavage substrate (FIG. 1). In wildtype *Pseudomonas* strains, PHBA is immediately converted to protocatechuate (PCA) as it is formed. The biochemistry of the enzymes involved in the upper pathway have been described for several *Pseudomonas* strains (Romine et al., supra).

Batch and Continuous Fermentations:

The present process uses a batch method of fermentation. A classical batch fermentation is a closed system where the composition of the medium is set at the beginning of the fermentation and not subjected to artificial alterations during the fermentation. Thus, at the beginning of the fermentation the medium is inoculated with the desired organism or organisms and fermentation is permitted to occur adding nothing to the system. Typically, however, a batch fermentation is "batch" with respect to the addition of carbon source and attempts are often made at controlling factors such as pH and oxygen concentration. In batch systems the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the medium. An advantage of the fed-batch system is that it is more amenable to the use of toxic or immiscible aromatic substrates such as toluene or p-cresol. Using a fed-batch system it is possible to maintain a steady concentration of substrate at non-toxic levels while accommodating maximum bioconversion of the substrate to product.

The production of PHBA from aromatic compounds such as toluene or p-cresol will be limited by the amount of the aromatic substrate and carbon sources added. In simple batch fermentation, production will be limited by the amount of toluene initially added. Since toluene is toxic and has limited solubility in water, its low initial concentration will govern the amount of PHBA produced. The ability to run the process at such a low toluene (i.e., 30–60 ppm) allows operation below a lower explosive limit which for toluene is 120 ppm. This low limit is a clear safety advantage to the process. Fed-batch techniques where the carbon source and toluene are added at rates which are similar to the utilization of these compounds will keep the toluene concentration in the medium low and can significantly increase the amount of PHBA produced.

Batch and fed-batch fermentations are common and well known in the art and examples may be found in, for example Brock, Thomas D. In *Biotechnology: A Textbook of Industrial Microbiology*, 2nd ed.; Sinauer Associates, Inc.: Sunderland, Mass., 1989 or Deshpande, Mukund V. *Appl. Biochem. Biotechnol.* 36:227 (1992).

Although the present invention is performed in batch mode, it is contemplated that the method would be adaptable to continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen source at low concentration and allow all other parameters to be in excess. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the fermentation. Methods of modulating nutrients and growth factors for continuous fermentation processes as well as techniques for maximizing the rate of product-formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for PHBA production.

Carbon Source:

A variety of carbon sources are suitable in the present invention and include but are not limited to materials (such as succinate, lactate, acetate, ethanol), monosaccharides (such as glucose and fructose), oligosaccharides (such as lactose or sucrose), polysaccharides (such as starch or cellulose), or mixtures thereof and unpurified mixtures from renewable feedstocks (such as cheese whey permeate, cornsteep liquor, sugar beet molasses, and barley malt). The needs of the desired production cell dictate the choice of the carbon substrate. For the purposes of the present invention, glucose is preferred.

Aromatic Substrates:

A variety of aromatic substrates may be used in the present invention, including but not limited to toluene, p-cresol, p-hydroxybenzyl alcohol, p-hydroxybenzaldehyde, and any aromatic compounds where the chemical structure is similar to toluene-and the intermediates of the TMO pathway (i.e., compounds that are subject to degradation by the TMO pathway).

The concentration of the aromatic substrate (such as toluene and p-cresol) and of the carbon source in the medium are limiting factors for the production of PHBA. Preferred concentrations of toluene are from about 30 ppm to about 500 ppm where a range of about 30 ppm to about 60 ppm is most preferred. There are tolerant strains that can ferment toluene at >500 ppm and there are sensitive strains that may operate at a more suitable range of 1–5 ppm. The preferred concentration of p-cresol for *Pseudomonas mendocina* is from about 1 mM to about 5 mM. More tolerant strains are expected as well as more sensitive strains. The p-cresol concentration needs to be adjusted accordingly.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Procedures for the genetic manipulations of cellular genomes are well known in the art. Techniques suitable for use in the following examples may be found in Sambrook, J. In *Molecular Cloning: A Laboratory Manual*, 2nd ed., Cold Spring Harbor Laboratory Press, 1989.

Materials and methods suitable for the maintenance and growth of bacterial cultures are well known in the art. Techniques suitable for use in the following examples may be found in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds.; American Society for Microbiology: Washington, D.C., 1994 or Brock, Thomas D. In *Biotechnology: A Textbook of Industrial Microbiology*, 2nd ed.; Sinauer Associates, Inc.: Sunderland, Mass., 1989. All reagents and materials used for the growth and maintenance of bacterial cells were obtained from Aldrich Chemicals (Milwaukee, WT), DIFCO Laboratories (Detroit, Mich.), GIBCO/BRL (Gaithersburg, Md.), or Sigma Chemical Company (St. Louis, Mo.) unless otherwise specified.

Materials and Growth Conditions

Cell Strains and Plasmids:

For General Use:
*Escherichia coli* DH5α (Clontech, Palo Alto, Calif.), *Escherichia coli* DH10B (Gibco BRL, Gaithersburg, Md.), *Escherichia coli* JM105 (ATCC 47016), *Escherichia coli* Top10F' (Invitrogen, Carlsbad, Calif. 92008) *Escherichia coli* XL 1-Blue MR (Stratagene, La Jolla, Calif.) and *Escherichia coli* XL2 Blue (Stratagene, La Jolla, Calif.).

Sources of DNA for Cloning:
*Pseudomonas mendocina* KR-1 (U.S. Pat. No. 5,171,684; Amgen, Thousand Oaks, Calif.), *Pseudomonas mendocina* KRC16 KDpobA51 (ATCC 55885) (PCT/US98/WO 12072; DuPont, Wilmington, Del.) and *Pseudomonas putida* (NCIMB 9869).

For Plasmid Mobilization:
*Escherichia coli* S17–1 (ATCC 47055).

For pcuC::lacZ Expression:
*Escherichia coli* MC1061 (CGSC 6649).

For p-Cresol Production:
*Escherichia coli* G1724 (Invitrogen, Carlsbad, Calif.), *Escherichia coli* JM105 (ATCC 47016) and *Pseudomonas putida* (ATCC 29607).

For PHBA Production:
*Agrobacterium rhizogenes* (ATCC 15834), *Pseudomonas mendocina* KRC16 KDpobA51 (ATCC 55885) (PCT/US98/12072; DuPont, Wilmington, Del.) and *Pseudomonas putida* (ATCC 29607).

For tmo and pcu-encoded Enzyme Synthesis:
*Pseudomonas putida* DOT-T1 (Ramos et al., J. Bact. 177(14):3911–3916 (1995)). *Pseudomonas putida* DOT-T1 C5aAR1 has mutations that inactivate toluene dioxygenase. *Pseudomonas putida* DOT-T1E (CECT 5312).

"ATCC" refers to the American Type Culture Collection international depository located at 10801 University Boulevard, Manassas, Va. 20110–2209, U.S.A. The designations refer to the accession number of the deposited material.

"CGSC" refers to the *E. coli* Genetic Stock Center located at 355 Osborn Memorial Laboratories, Department of Biology, Yale University, New Haven, Conn. 06520–8104. The designations refer to the accession number of the deposited material.

"NCCB" refers to the Netherlands Culture Collection of Bacteria, Utrecht University, P.O. Box 80.056, 3508 TB Utrecht, the Netherlands. The designations refer to the accession number of the deposited material.

"NCIMB" refers to the National Collection of Industrial and Marine Bacteria Ltd located at 23 St. Machar Drive, Aberdeen, AB2 1RY, U.K. The designations refer to the accession number of the deposited material.

Growth Conditions:

Typically, studies were conducted by shaking cultures in 125 mL or 250 mL flasks. Experiments using toluene were conducted in 125 mL sealed flasks. Minimal (lean) medium with glucose as the carbon source and ammonia as the nitrogen source was used most extensively. Yeast extract, when added to obtain a "rich" medium, was at 0.5–1.0 g/L. Some of the PHBA production examples included two stages, where the cells were first grown to a suitable cell density in minimal medium containing glucose, followed by transfer to a production medium containing an aromatic substrate for PHBA production. Culture conditions were modulated according to the method of growth and optimized for the production of PHBA. The pH of the cultures should be maintained within a range of about from 6.3 to 7.9. A range of about 7.2 to 7.7 is most preferred. Other media amenable to the procedures of the present invention are common in the art and are fully described in *Manual of Methods for General Bacteriology* (P. Gerhardt, R. G. E. Murray, R. N. Costilow, E. W. Nester, W. A. Wood, N. R. Krieg and G. B. Phillips, Eds.; American Society for Microbiology: Washington, D.C., 1994).

Example 1

Cloning and Sequencing of the *Pseudomonas mendocina* pcu Operon Preparation of Genomic DNA

*Pseudomonas mendocina* KRC16 KDpobA51 (ATCC 55885) containing an omega-disrupted pobA-1 gene was used as the source of genomic DNA. The cells of a 50 mL overnight stationary phase culture were collected by centrifugation at 6,000 rpm, 4° C. for 10 min. The supernatant was decanted and the pellets resuspended with 5 mL TEG (25 mM Tris-HCl, 10 mM EDTA, 50 mM glucose, pH 8.0). About 1.5 mL of RNAse (100 µg/mL) was added into the mixture. The sample was kept at room temperature for 5 min, and then extracted twice with an equal volume of phenol. The two phases were separated by a centrifugation at 6,000 rpm for 10 min. The aqueous phase was extracted twice with phenol:chloroform (1:1). Two volumes of 100% ethanol were added to the aqueous phase to precipitate DNA. After 20 min the solution was centrifuged at 10,000 rpm, and the pellet was collected, dried, and resuspended in 2 to 5 mL TE buffer. The DNA sample was dialyzed against TE buffer at 4° C. overnight.

Construction of a Genomic Library:

10 µg of genomic DNA was digested with 100 units of BstYI restriction endonuclease at 60° C., and samples removed at 2, 5, 10, 20 and 30 min intervals in order to obtain partially digested DNA. The pooled partial digests were treated with phenol:chloroform (1:1), chloroform, and two volumes ethanol added to precipitate the DNA. Resuspended DNA (1.6 µg) was ligated at 4° C. overnight using T4 DNA ligase and <1 µg SuperCos 1 (Stratagene, LaJolla, Calif.) that had been digested with XbaI, dephosphorylated with CIP, and then digested with BamHI. Each enzyme treatment was followed by extraction with equal volumes of phenol:chloroform (1:1), chloroform, and precipitated with 2 volumes of ethanol. Ligated DNA was recovered in bacteriophage lambda by in vitro packaging using a Gigapack II Gold Packaging Extract (Stratagene, La Jolla, Calif.).

Selection of Clones with a pobA-1 Omega Insert:

*Escherichia coli* XL 1-Blue MR cells were infected with the packaged cosmid library and plated on LB medium containing 50 mg/L amp and 25 mg/L strep, and cultured at 37° C. overnight. As a control, part of the packaged library was plated on LB medium containing 50 mg/L amp to determine total number of cosmid containing cells. About 1% of the amp resistant colonies were also strep resistant, and these represented clones that had acquired the omega-inactivated (strR)pobA-1 gene.

Restriction and Hybridization Analysis of strR Cosmids:

Plasmids were isolated from 5 mL cultures of strR clones using an alkaline lysis method (Bimboim et al., *Nucleic Acids Res.* 7(6):1513–1523 (1979)). The plasmids were digested with the restriction enzymes HindIII or ClaI and fragments separated by electrophoresis overnight on a 0.7% agarose gel in TBE buffer (89 mM Tris-borate, 89 mM boric acid, 2 mM EDTA). Cosmids were identified by the presence of a 14 kb HindIII fragment, or a 12.5 kb ClaI fragment as predicted (Wright et al., *Appl. Environ. Microbiol* 60(1): 235–242 (1994)). DNA was transferred from the agarose gel to a GeneScreen Plus nylon membrane (NEN Life Science Products, Boston, Mass.) using a VacuGene XL system (Pharmacia Biotech, Piscataway, N.J.). Depurination of DNA in the gel with 0.25 M HCl for 7 min was followed by denaturation with 1.5 M NaCl+0.5 M NaOH for 7 min, neutralization with 1.0 M Tris-HCl pH 7.5+1.5 M NaCl for 7 min, and transfer to membrane in 20×SSC for 30 min. The nylon membrane was removed, washed in 0.4 M NaOH (1 min), in 0.2 M Tris-HCl pH 7.5+1×SSC (1 min), in 2×SSC (1 min), followed by exposure to ultraviolet light for about 2 min to produce nucleic acid crosslinking.

The membrane was prehybridized for 1 h at 65° C. in a hybridization solution containing 5×SSC, 0.1% (w/v) SDS, 0.5% (w/v) blocking reagent (NEN Life Science Products, Boston, Mass.) and 5% (w/v) Dextran Sulfate. The hybridization probe was a heterologous sequence for the cytochrome c subunit of PCMH from *Pseudomonas putida* NCIMB 9869. The cytochrome c subunit gene (pchC) was cloned from DNA purified from *Pseudomonas putida* NCIMB 9869 by CsCl-ethidium bromide centrifugation (Pemberton et al., *J. Bact.* 114(1):424–433 (1973)), and amplified by PCR using primers (SEQ ID NO:78 and SEQ ID NO:79) based on the published sequence (Kim et al., *J. Bact.* 176(20):6349–6361 (1994)). The 100 μL PCR reaction mixture contained: 0.5 mM dNTPs, reaction buffer (final concentration of 10 mM Tris-HCl, pH 8.3, 50 mM KCl, 1.5 mM $MgCl_2$, and 0.01% gelatin), 0.1 mg of *Pseudomonas putida* genomic DNA, and 1 unit of Taq DNA polymerase. The DNA sample was denatured at 94° C. for 1 min, and annealed at 50° C. for 2 min. Polymerization was performed at 74° C. for 2 min with an increased extension time of 5 sec per cycle. The polymerase chain reaction was accomplished by 25 cycles. The PCR DNA fragment was detected and analyzed by electrophoresis on 1% agarose gels with 0.5 mg/L ethidium bromide, and cloned into the vector pUC18 (Pharmacia Biotech, Piscataway, N.J.).

For ease of identification, the pchC DNA was labeled with a fluorescein nucleotide in a 30 μL reaction mixture containing a random primer, reaction buffer, fluorescein nucleotide mix (NEN Life Science Products, Boston, Mass.) and Klenow enzyme at 37° C. for 1 h. The labeled probe was then hybridized to the membrane-bound genomic DNA in the same buffer for 16 h at 65° C.

After hybridization, the membrane was washed for 15 min in 2×SSC, 0.1% SDS, followed by a second 15 min wash in 0.2×SSC, 0.1% SDS at 65° C. The membrane was blocked for 1 h in buffer containing 0.5% blocking reagent and then incubated with antifluorescein-horse radish peroxidase conjugate (1:1000) (NEN Life Science Products, Boston, Mass.) at room temperature for 1 h.

After the incubation the membranes were washed four times for 5 min with 0.1 M Tris-HCl pH 7.5, 0.15 M NaCl, and incubated in a chemiluminescence reagent (Renaissance nucleic acid chemiluminescent reagent, NEN Life Science Products, Boston, Mass.) for 1 min at room temperature, and then exposed to Reflection autoradiography film (NEN Life Science Products, Boston, Mass.). Those clones having both the correct restriction pattern with HindIII or ClaI, and which hybridized to the pchC probe, were selected for sub-cloning and sequencing.

Subcloning and Sequencing:

A strR cosmid was digested with HindIII and the ~14 kb insert isolated from a 0.8% agarose gel using the DNA preparation kit GeneClean (Bio101, Vista, Calif.). The isolated fragment was cloned into the HindIII site of the vector pZErO-1 (Invitrogen, Carlsbad, Calif.), transformed into *Escherichia coli* Top10F', and selected on LB medium containing 50 mg/L zeocin. Zeocin-resistant clones were screened by digestion of plasmid minipreps with HindIII, BamHI, SalI/BamHI, ClaI/SphI, and SphI. A plasmid with a digestion pattern indicating that the pcu-encoded enzymes were oriented for transcription by the lac promoter of pZErO-1 was designated pPCU1, and a plasmid with the opposite orientation was designated pPCU2.

A 3.5 kb NruI/EcoRI fragment was isolated from pPCU1, and a BamHI adaptor (New England Biolabs, Beverly, Mass.) annealed and ligated to 2 μg of fragment in a 20 μL reaction containing 2 mM adaptor at 16° C. for 16 h. Following a phenol:chloroform (1:1) extraction and ethanol precipitation, the DNA was dissolved in 12 μL TE, digested with BamHI for 5 h, and purified by electrophoresis on a 1% agarose gel and isolated with GeneClean as before. The BamHI/EcoRI fragment was cloned into the EcoRI/BamHI digested vector pK194 (ATCC 37767) to yield plasmid pPCU3. The complete sequence of the pcu operon is shown in SEQ ID NO:1 and the nucleotide sequences for the transcriptional activator PcuR (SEQ ID NO:98), PHBAD (SEQ ID NO:99), the two subunits of PCMH (SEQ ID NO:100 and SEQ ID NO:102), and an unidentified open reading frame (SEQ ID NO:101). Also given are the predicted amino acid sequences for the transcriptional activator PcuR (SEQ ID NO:2), PHBAD (SEQ ID NO:3), the two subunits of PCMH (SEQ ID NO:4 and SEQ ID NO:6), and an unidentified open reading frame (SEQ ID NO:5). The DNA was sequenced with synthetic primers (SEQ ID NO:7 to SEQ ID NO:77) according to standard methods.

Figure 2:
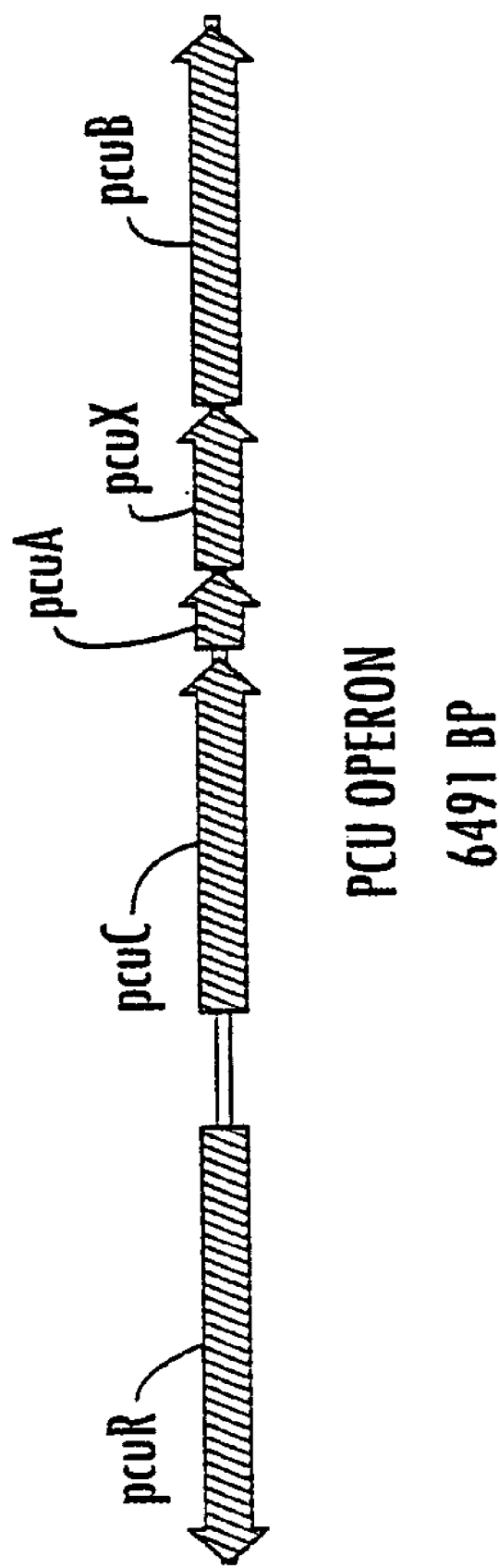
FIG. 2 illustrates *Pseudomonas mendocina* KR-1 pcu operon.

Identification of the PHBAD and PCMH coding sequences was based on percent homology to the corresponding predicted amino acid sequences for these enzymes from *Pseudomonas putida* NCIMB 9866 and 9869 (Kim et al., supra; Cronin et al., *DNA Sequence* 10(1):7–17 (1999)). Identification of the PcuR transcriptional activator was based on homology to the predicted amino acid sequence of the TbuT transcriptional activator of *Ralstonia pickettii* (Olsen et al., *J. Bacteriol.* 176(12):3749–3756 (1994)). Based on the work of Cronin et al. (supra), the unidentified open reading frame (SEQ ID NO:5) may be an inner membrane protein. Their analysis by PSORT for the *Pseudomonas putida* protein predicts it to be an inner membrane protein, and analysis by TMpred predicts it to have one or two transmembrane helices, with the bulk of the protein lying on the cytoplasmic side in either situation. The arrangement of genes in the pcu operon is illustrated in FIG. 2. The best homologies to each ORF, and thus their putative function in the pcu operon, are listed in Table 1.

| ORF | Similarity Identified | SEQ ID base | SEQ ID Peptide | % Identity[a] | % Similarity[b] | E-value[c] | Citation |
|---|---|---|---|---|---|---|---|
| 1.1 | gi|1657782 transcriptional activator TbuT (*Ralstonia pickettii*) | 98 | 2 | 48% | 63% | 1e−143 | J. Bacteriol. 176(12), 3749–3756 (1994) |
| 1.2 | gb|AAA75634.2| p-hydroxybenzaldehyde dehydrogenase(*Pseudomonas putida*) | 99 | 3 | 75% | 83% | | DNA Seq. 10(1), 7–17 (1999) |
| 1.3 | gb|AAA80319.2| p-cresol methylhydroxylase, cytochrome subunit precursor (*Pseudomonas putida*) | 100 | 4 | 60% | 74% | 3e−25 | DNA Seq. 10(1), 7–17 (1999) |
| 1.4 | gb|AAD29836.1|U96338_3 unknown (*Pseudomonas putida*) | 101 | 5 | 46% | 61% | 5e−36 | DNA Seq. 10(1), 7–17 (1999) |
| 1.5 | gb|AAA80318.2| p-cresol methylhydroxylase, flavoprotein subunit (*Pseudomonas putida*) | 102 | 6 | 78% | 88% | | DNA Seq. 10(1), 7–17 (1999) |
| 2.1 | emb|CAB43725.1| membrane protein (*Pseudomonas putida*) | 103 | 92 | 81% | 87% | | Gene 232, 69–76 (1999) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Example 2

Cloning the *Pseudomonas mendocina* tmo Operon

*Pseudomonas mendocina* KR-1 was the source of total genomic DNA, and it was isolated as described before for *Pseudomonas mendocina* KRC16KDpobA51(ATCC 55885). Total genomic DNA was digested with SstI+XmaI, separated on a 0.8% low-melting agarose gel, and fragments in the 5–7 kb size range recovered. The purified DNA was ligated to the vector pUC 18 that had been digested with SstI+XmaI, and the ligated DNA transformed into *Escherichia coli* JM105. Clones were selected on LB plates containing amp (100 mg/L) and 10 mM tryptophan. *Escherichia coli* is able to produce indole from tryptophan using tryptophanase, and the tmo-encoded toluene monooxygenase converts the indole to cis-indole-2,3-dihydrodiol, which then forms indoxyl through the spontaneous elimination of water, and is then oxidized by air to indigo. An indigo-producing colony was isolated and the correctly configured plasmid identified as pTMO1.

Example 3

Construction of pcu and pcu/tmo Expression Plasmids

Construction of the pcu plasmid pPCU12 pPCU1 was digested with NruI+ApaI and a 2.4 kb fragment was isolated by electrophoresis on a 1% agarose gel and purified using a GeneClean kit, then ligated to the SmaI+ApaI digested vector pGadGH (Clontech, Palo Alto, Calif.). The ligation was transformed into competent *Escherichia coli* strain DH5α, and transformants were isolated on LB+amp (100 mg/L) plates. The correct construct, which was identified by the band patterns produced with HindIII+BamHI or BamHI+SalI digests, was named pPCU9.5. Next, a 2.6 kb ApaI fragment was isolated from pPCU1 by electrophoresis on a 1% agarose gel followed by purification with GeneClean as before. This fragment was cloned into ApaI-digested pPCU9.5 which had also been treated with CIP. Clones containing the inserted fragment were distinguished by digestion with ApaI and detected the presence of the 2.6 kb fragment. The orientation of the insert was determined by the fragmentation pattern of a BglII digest. The plasmid with the pattern indicating a complete pcu operon was named pPCU10.

The ~5 kb BamHI+HindIII fragment from pPCU10 was isolated as before and ligated into the BamHI+HindIII sites in the vector pK184 (ATCC 37766). The ligation was transformed into ultracompetent XL2 Blue cells. Transformants were selected using LB+kan (50 mg/L) plates. EcoRI and BglII digests were used to determine the correct construct, which was named pPCU11. The 5 kb BamHI+HindIII fragment was isolated from pPCU11 as described above, and the single-stranded ends were converted to double strands with the Klenow fragment of DNA polymerase I. The vector pRK310 (Ditta et al., *Plasmid* 13:149–153 (1985)) was digested with HindIII, and the single-stranded ends were also treated with the Klenow fragment of DNA polymerase I and then phosphatased with CIP. The two fragments were ligated together and electroporated into Electromax DH10B cells. Colonies with plasmids were selected on LB+tet (12.5 mg/L) plates. EcoRI and SalI digests of plasmids from the colonies were used to identify a clone of the correct construction, named pPCU12.

Construction of the pcu Plasmid pPCU18:

A 7.5 kb MluI+NheI pPCU1 fragment was isolated through agarose gel electrophoresis followed by purification with GeneClean. It was ligated into the MluI+NheI sites of plasmid pSL1180 (Pharmacia Biotech, Piscataway, N.J.). The ligation was transformed into competent DH5α cells.

Transformants were identified by growth on LB+amp (100 mg/L) plates. SalI digests indicated the correct construct, which was named pPCU17. Plasmid pPCU17 was digested with BamHI+HindIII, and the 7.5 kb piece of DNA with the pcu genes was isolated as described earlier. The fragment was cloned into the BamHI+HindIII sites of the vector pGV1120 (Leemans et al., Gene 19:361–364 (1982)). Electrocompetent *Pseudomonas putida* strain DOT-T1 C5aAR1 cells were electroporated with the ligated DNA. Cells were selected on LB+strep (50 mg/L) plates at 30° C. overnight. Plasmids were isolated from clones grown on the plates and digested with EcoRI. The plasmid with the correct digest pattern was named pPCU18.

Construction of pcuC::lacZ Fusion Plasmids pPCUR1 and pPCUR2:

The non-translated pcu promoter region between pcuR and pcuC was amplified by PCR in order to construct a lacZ fusion to examine regulation of the pcu operon. The reaction contained the following: 0.5 μL pPCU1 (0.8 μg/μL), 1 μL primer PCUR1L (10 pmol/μL) (SEQ ID NO:95), 1 .μL primer PCUR2L (10 pmol/μL) (SEQ ID NO:96), 33.3 μL water, 2.2 μL 25 mM Mg(OAc)$_2$, 1 μL 10 mM dNTPs, 10 μL 5×GC Genomic PCR Reaction Buffer, and 1 μL Advantage-GC Genomic Polymerase Mix (50×). The last four components were from the Advantage-GC Genomic PCR Kit (Clontech, Palo Alto, Calif.). The reaction was put through the following thermocycles: 1 min at 94° C., then 30 cycles of 30 sec at 94° C., 4 min at 68° C., and incubation at 4° C. overnight. The PCR product was purified using GeneClean, digested with BamHI and isolated as a 2.4 kb fragment following electrophoresis on a 0.6% agarose gel. The fragment was ligated to the vector pMC1403 (NCCB no. PC-V3088), which had been digested with BamHI and dephosphorylated with SAP. The ligation was transformed into competent *Escherichia coli* MC1061 cells. Transformants were selected on LB+Amp (100 mg/L) plates. The orientation of the insert in the vector was determined by SstI and PstI digests, and a plasmid where the ribosome binding site and AUG initiation codon from pcuC was fused to the lac operon was named pPCUR1. A control plasmid with the PCR product cloned in the opposite orientation was named pPCUR2.

Figure 3:
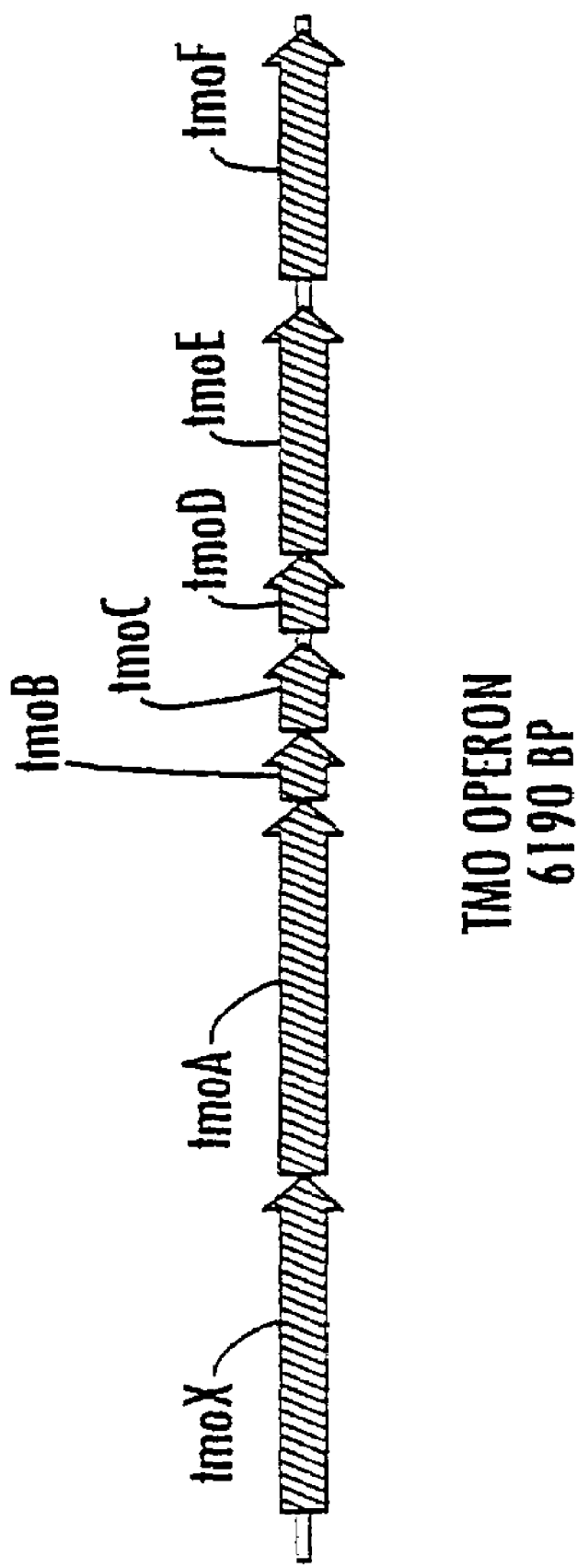
FIG. 3 illustrates *Pseudomonas mendocina* KR-1 tmo operon.

Construction of the tmo Plasmid pTMO3:

The vector pLEX (Invitrogen, Carlsbad, Calif.) was digested with SphI+SstI and ligated to a 6 kb tmo fragment from pTMO1 (FIG. 3) digested with the same enzymes. Ligated DNA was transformed into *Escherichia coli* strain G1724 (Invitrogen, Carlsbad, Calif.) and selected on LB+amp (100 mg/L). A plasmid with tmo under the transcriptional control of the $P_L$ promoter was designated pTMO3.

Construction of the tmo Plasmid pTMO9:

Plasmid pTMO1 was digested with HindIII+BglII. The 960 bp fragment was isolated and purified with GeneClean, and ligated to HindIII+BglII cut plasmid pSL1180 (Pharmacia, Piscataway, N.J.). The ligation was used to transform competent *Escherichia coli* XL2 Blue cells, which were then incubated on LB+amp (100 mg/L) plates. HindIII digests and NcoI digests of the plasmids from transformants identified those with the correct insert. A correct plasmid was named pTMO6. The 960 bp SmaI+HindIII fragment from pTMO6 was isolated and purified as before and ligated to the vector pMMB208 (ATTC 37810) which had been digested with SmaI+HindIII. Competent XL1 Blue cells were transformed with the ligated DNA and spread onto LB+chl (50 mg/L) plates. HindIII+SstI digests of plasmids from transformants were used to determine clones with the proper constructs, which were named pTMO7. Next, a 5 kb piece of DNA was isolated from pTMO1 by BglII+BamHI digestion and inserted into the BamHI site of pTMO7. The ligated DNA was transformed into competent XL1 Blue cells, which were then spread onto LB+chl (50 mg/L) plates and incubated at 37° C. until colonies were apparent. After a few days at 4° C., some of the colonies on the plates developed an indigo-blue color. Plasmids were isolated from indigo-blue colonies and digested with HindIII to confirm the presence of a correctly constructed plasmid, which was named pTMO8. The 1.2 kb kan resistance marker from pUC4K (Pharmacia, Piscataway, N.J.) was isolated by EcoRI digestion, gel electrophoresis, and GeneClean purification. It was ligated to EcoRI cut and SAP treated pTMO8, then transformed into competent XL1 Blue cells. The correct plasmid from a clone that grew on LB+kan (50 mg/L)+chl (50 mg/L) plates was named pTMO9.

Construction of the tmo Plasmids pTMO17 and pTMO18:

A BamHI digest of pTMO11 and a BglII digest of the vector pGV1120 (Leemans et al., *Gene* 19:361–364 (1982)) were electrophoresed on a 0.8% agarose gel. The 6 kb pTMO11 fragment and the vector fragment were excised and purified using a GeneClean kit. The two pieces were ligated together, transformed into competent *Escherichia coli* DH5α cells, and spread onto LB+tet (10 mg/L) plates. The plasmids from selected colonies were digested with HindIII, and one with the correct pattern of bands was named pTMO17.

A 7.5 kb BamHI pTMO15 fragment and a BglII fragment from the vector pGV1120 were gel-purified as described earlier. They were ligated together, transformed into *Escherichia coli*, and plated on LB+tet (10 mg/L) plates. HindIII digests of the plasmids from transformants were used to identify constructs containing the tmo operon, and a correctly configured plasmid was named pTMO18.

Construction of the Expression Plasmid pMC3 Containing pcu and tmo:

The pcu operon (pcuC through pcuB) was amplified in a PCR reaction containing 4 μL dNTPs (2.5 mM), primer PCUAMP1 (10 pmol/μL) (SEQ ID NO:93), primer PCUAMP2 (10 pmol/μL) (SEQ ID NO:94), 30.7 μL water, 0.3 μL pPCU10 (0.3 μg), 2 μL Buffer A, 8 μL Buffer B, and 1 μL Elongase (the last 3 components were from the Elongase amplification system (Gibco BRL, Gaithersburg, Md.). The cycles used were as follows: 30 sec at 94° C., then 35 cycles of (45 sec at 94° C., 30 sec at 55° C., 5 min at 68° C.), finally 4° C. overnight. The ~5.5 kb product was purified using a GeneClean kit, digested with HindIII, isolated from a 0.8% agarose gel, and purified again with GeneClean. This fragment was inserted into a HindIII digested and phosphatased (using CIP) pUC 18 vector. The ligation was transformed into competent *Escherichia coli* XL1 Blue cells, and transformants were selected on LB+amp (100 mg/L)+IPTG (1 mM)+X-gal (5-bromo-4-chloro-3-indolyl-β-D-galactoside) (50 mg/L) plates. White colonies indicated the presence of an insert in the vector. The correct construct, which was named pPCU14, was found by observing HindIII digest patterns of the plasmids isolated from white transformants. Orientation of the inserts was determined by PstI digest patterns.

To remove the BamHI site in vector pRK310, the single-stranded ends created by a BamHI digest of pRK310 were removed using mung bean nuclease. The vector was then allowed to self-ligate and the product was electroporated into *Escherichia coli* Electromax DH10B cells. The cells were spread onto LB+tet (12.5 mg/L) plates to select for those containing plasmids. BamHI+BglII digests were used to identify clones that had the correct construct, which was named pRK310BamKO. This new vector was digested with HindIII and phosphatased with SAP. The 5.5 kb HindIII fragment of pPCU14, isolated as described previously, was ligated into the vector pRK310BamKO. Electromax DH10B cells were electroporated with the ligated DNA. Plasmids were isolated from cells that grew on LB+tet (12.5 mg/L) plates and were digested, first with HindIII to ascertain the presence of an insert, then with SalI to determine the orientation of the insert. The correct plasmid was named pPCU16.

The 1.2 kb kan resistance marker from the vector pUC4K (Pharmacia Biotech, Piscataway, N.J.) was isolated as an EcoRI fragment in the manner described above, and inserted into the EcoRI site of pTMO1. The ligation was transformed into competent XL1 Blue cells, which were then spread onto LB+kan (50 mg/L)+amp (100 mg/L)+IPTG (1 mM) plates. Indigo-blue colonies were diagnostic for the presence of the tmo operon because tmo-encoded toluene monooxygenase catalyzes, in part, the formation of indigo from indole. The correct construct, which was named pTMO11, was ascertained through the digestion of the transforming plasmids with BamHI. The 5.9 kb pTMO11 fragment containing the tmo genes was purified as described previously, and was ligated to BamHI cut and SAP-phosphatased pPCU16. The ligated DNA was electroporated into Electromax DH10B cells, which were then spread onto LB+tet (12.5 mg/L)+IPTG (1 mM) plates. Transformants that carried plasmids with the tmo genes were indigo-blue, as described before. The correct construct was identified by digestion with PstI, and was named pMC3.

Construction of the Expression Plasmid pMC4 Containing pcu and tmo:

*Pseudomonas mendocina* KR-1 genomic DNA was digested to completion with EcoRI. The digested DNA was run on a 0.8% agarose gel, and DNA larger than ~6 kb was cut out of the gel and purified with GeneClean. Plasmid pUC18 was digested with EcoRI and the ends were phosphatased with SAP. The genomic DNA pieces were ligated to the vector, then electroporated into *Escherichia coli* Electromax DH10B cells. The cells were incubated on LB+amp (100 mg/L)+IPTG (1 mM) plates. Plasmids were isolated from indigo-producing transformant colonies and digested with EcoRI. The plasmid with the correct digest pattern was named pTMO14. A 7.3 kb SmaI fragment from pTMO14 was isolated as before and cloned into the 2.7 kb HincII cut and SAP treated pUC4K vector. The ligation was used to electroporate electrocompetent *Escherichia coli* DH5α cells, which were then incubated on LB+amp (100 mg/L)+IPTG (1 mM) plates. BamHI digests were performed on plasmids from indigo-blue colonies from the plates. The correct construct, which had the tmo operon flanked by BamHI sites, was named pTMO15.

Figure 4:
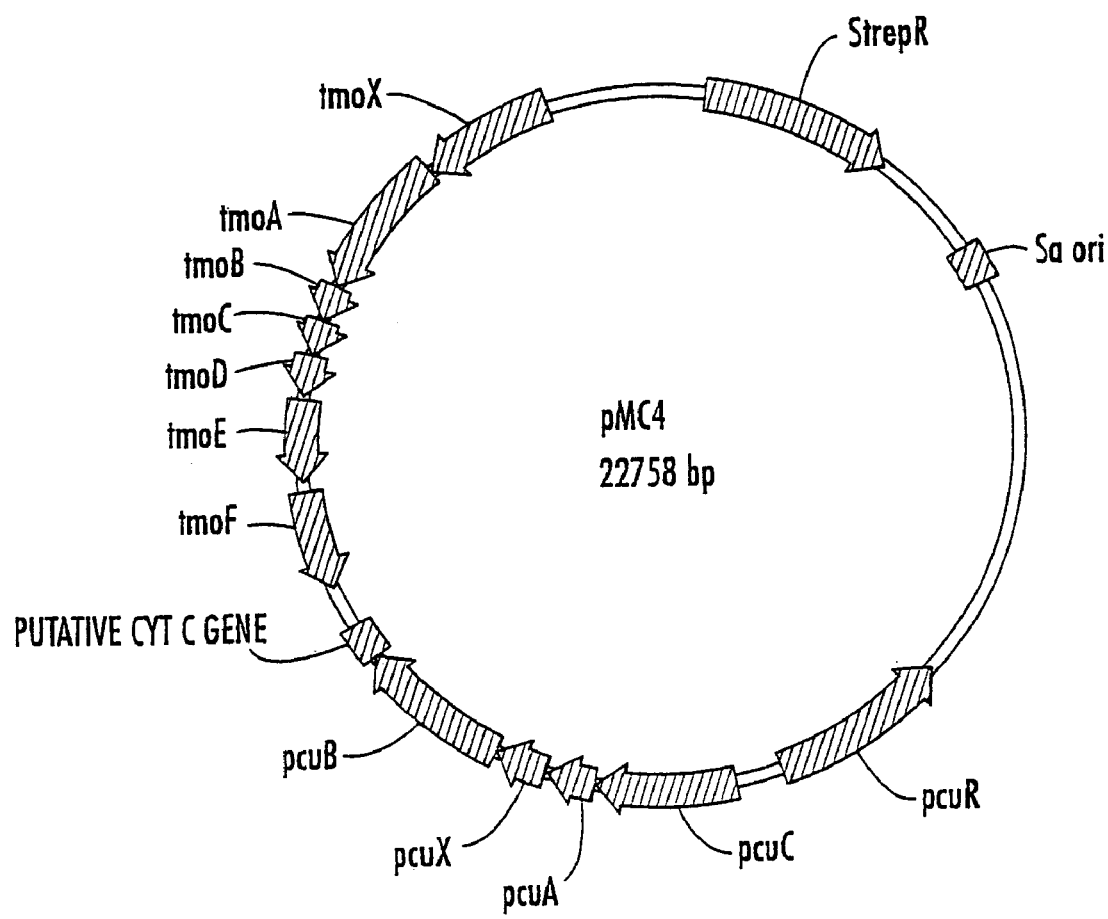
FIG. 4 illustrates the pcu and tmo expression plasmid pMC4.

The 7.3 kb BamHI pTMO15 fragment was isolated as before and inserted into the BamHI site of pPCU18. This ligated DNA was electroporated into electrocompetent *Pseudomonas putida* DOT-T1 C5aAR1 cells, which were incubated on LB+strep (50 mg/L)+indole (1 mM) plates. Some of the plates also had a drop of toluene added to the inside of the top lid. They were all incubated at 30° C. overnight. PstI digests of plasmids from transformants identified one that had both pcu and tmo operons, and this clone was named pMC4 (FIG. 4). Plasmid pMC4 was deposited with the ATCC under accession number PTA-4775 on Oct. 24, 2002 in accordance with the terms of the Budapest Treaty.

Example 4

Production of p-Cresol from Toluene in *Escherichia coli*

*Escherichia coli* strain JM105 harboring plasmid pTMO1, which places tmo expression under control of the lac promoter, was grown under inducing conditions in the presence of 1 mM IPTG, or under non-inducing conditions in the absence of IPTG. *Escherichia coli* strain G1724 harboring plasmid pTMO3, which places tmo expression under control of the PL promoter, was grown under inducing conditions in the presence of 100 mg/L tryptophan, or under non-inducing conditions in the absence of tryptophan.

Induced or non-induced cell samples were resuspended in minimal medium at a concentration of 100 mg/mL. To 26 mL of minimal medium in a 125 mL sealed flask was added 4 mL of the cell suspension, and 1 mL of toluene placed in a center well. Following a 36 h incubation 15 mL of the cells were acidified, extracted with ethyl acetate, and analysed by GC/MS. Table 2 shows that p-cresol is produced when induced cells harboring either plasmid pTMO1 or plasmid pTMO3 are incubated in the presence of toluene. In contrast, in the absence of induction of tmo using either plasmid, no p-cresol is detectable.

TABLE 2

| Plasmid | Inducer | GC Peak Area |
|---------|---------|--------------|
| pTMO1 | IPTG | $1.45 \times 10^6$ |
| pTMO1 | None | 0 |
| pTMO3 | Tryptophan | $5.05 \times 10^5$ |
| pTMO3 | None | 0 |

Example 5

Bioconversion of Toluene to p-cresol in *Pseudomonas putida* ATCC 29607

*Pseudomonas putida* ATCC 29607 was transformed with pTMO9 and pPCU12, grown at 30° C. and 250 rpm in medium A (Table 3). At an $OD_{600}$ of 1.98 (16 h) cells were harvested and washed in MM#4 medium (Table 4). (Trace elements found in both medium A and MM#4 Medium are listed in Table 5.) PHBA production was carried out in 125 mL sealed flasks in 5 mL MM#4 medium that contained 0.5 $OD_{600}$ cells, 0.05 mM $MgSO_4$, 2 mM glucose, 1 mM IPTG, 0.1 M HEPES buffer pH 7.5–8.0 and 60 ppm toluene. The flasks were incubated shaking at 250 rpm and 30° C. A non-induced control did not have IPTG added. Samples were incubated for 6 h, and the presence of p-cresol detected by HPLC. In the presence of IPTG 0.93 mM p-cresol was present after 6 h, compared to 0.135 mM in the non-induced sample.

TABLE 3

| | Medium A | |
|---|---|---|
| | per L | Special Conditions |
| $KH_2PO_4$ | 1.2 g | |
| $(NH4)_2SO_4$ | 3 g | |
| glucose | 7 g/L | sterilized separately |
| $MgSO_4 \cdot 7H_2O$ | 0.15 g | |
| trace elements | 10 mL | sterilized separately |
| HEPES | 0.05 M | |
| yeast extract | 1 g | sterilized separately |

Titrate to pH 7.2 with KOH or $H_2SO_4$

TABLE 4

MM #4 Medium

| | |
|---|---|
| trace elements | 10 mL |
| yeast extract | 0.48 g |
| MgSO$_4$•7H$_2$O | 10 mM |
| NaKPO$_4$ | 25 mM |
| DD H$_2$O | 1 L |
| PH | 7.2 |

TABLE 5

Trace Elements in Medium A and MM#4

| | g/L |
|---|---|
| citric acid | 10 |
| CaCl$_2$•2H$_2$O | 1.5 |
| FeSO$_4$•7H$_2$O | 2.8 |
| ZnSO$_4$•7H$_2$O | 0.39 |
| trace elements | |

| Medium A and MM#4 | g/l |
|---|---|
| CuSO$_4$•5H$_2$O | 0.38 |
| CoCl$_2$•6H$_2$O | 0.2 |
| MnCl$_2$•4H$_2$O | 0.3 |

Example 6

Identification and Sequence of a tmo Regulatory Region

Detection of a Regulatory Sequence

Plasmids pTMO17 and pTMO18 differ in the amount of tmo sequence information that is present. Plasmid pTMO17 contains the six toluene monooxygenase genes tmoA-F. Plasmid pTMO18 also contains tmoA-F, but in addition has 1326 bp of DNA sequence information upstream from the translational initiation codon of tmoA. Plasmids pTMO17 and pTMO18 were transformed separately into *Pseudomonas putida* DOT-T1 C5aAR1 and selected on LB+strep (100 mg/L). Colonies were inoculated into 25 mL LB+1 mM indole+strep (100 mg/L) and shaken in a 125 mL baffel flask at 200 rpm and 30° C. until indigo production occurred. A 5 mL sample of cell suspension was extracted twice with an equal volume of ethyl acetate to solubilize the indigo, the two extracts were combined and the absorption at 600 nm recorded. A standard curve prepared with pure indigo in ethyl acetate was used to determine amounts in cell extracts.

TMO enzyme assays were carried out in a separate experiment using the same plasmids and strain. TMO was measured spectrophotometrically using a coupled assay, linking phenazine ethosulfate (PES) oxidation to reduction of 2,6-dichlorophenol-indophenol (DCPIP) as measured by a decrease in absorption at 600 mm ($E_{600nm}$=21,000 M$^{-1}$ cm$^{-1}$). The assay was initiated by the addition of enzyme to a 2.0 mL reaction mixture containing 0.67 µmol PES, 0.1 µmol DCPIP, 1.0 µmol toluene and saturating levels of purified p-cresol methylhydroxylase.

Table 6 shows that the presence of additional DNA upstream of tmoA enhances the level of TMO activity, which leads to a considerable improvement in indigo production.

TABLE 6

| Plasmid | TMO activity | Indigo produced (mg/L) |
|---|---|---|
| pTMO17 | 0.7 | 2.5 |
| pTMO18 | 1.3 | 88.0 |

Sequence of tmoX and its Upstream Promoter Region:

The DNA upstream of tmoA was sequenced with synthetic primers (SEQ ID NO:80 to SEQ ID NO:90) according to standard methods. The complete sequence of the DNA has the sequence found in SEQ ID NO:91. Encoded within the sequence is a protein, TmoX, with the initiator methionine at nucleotide 192 and a TAA translation terminator at position 1560. The predicted amino acid sequence of TmoX is given as SEQ ID NO:92 and its nucleotide sequence is in SEQ ID NO:103. TmoX has an 81% identity (87% similarity) in its predicted amino acid sequence compared to that of the TodX protein of *Pseudomonas putida* DOT-T1 (Table 1). TodX has been described as an outer membrane protein that may be involved in facilitating the delivery of exogenous toluene inside cells (Wang et al., *Mol Gen. Genet.* 246: 570–579 (1995)), but has also been linked to the signal transduction process which results in specific response of a tod promoter to toluene (Lau et al., *Proc. Natl. Acad. Sci. USA* 94:1453–1458 (1997)).

The tmoX promoter was identified by primer extension using a 23-mer oligonucleotide (SEQ ID NO:97) complementary to the DNA coding strand. The first nucleotide of the primer corresponded to a nucleotide 200 bp downstream from the A of the ATG initiation codon of the tmoX gene. *Pseudomonas mendocina* KR-1 was grown overnight in M9 minimal medium with 10 mM citrate as the sole carbon source. To 200 mL of fresh medium was added 5 mL of overnight culture to give an initial OD of about 0.2 at 660 nm. The culture was incubated at 30° C. on a rotary shaker to an OD of 0.8 at 660 nm. Aliquots of 20 mL were supplemented with either 1 mM p-cresol, toluene in the gas phase, or a control with no additions. Samples were used for RNA isolation at 30, 60 and 180 min after addition of the effector.

The primer (SEQ ID NO:97) was labeled at its 5' end using $^{32}$P-γ-ATP and polynucleotide kinase. To 30 µg of total RNA for each sample were added 10$^5$ CPM of labeled primer, which was extended using reverse transcriptase. The resulting cDNA was separated on a urea-polyacrylamide sequencing gel. In addition, the labeled primer was used to establish a sequencing ladder to facilitate the identification of the transcription initiation point. It was established that the 260 base cDNA product positioned the tmoX transcription initiation point as a G located 60 bp upstream of the A of the ATG translation initiation codon of tmoX. Analysis of the region upstream of the ATG codon shows the presence of a prokaryotic Shine-Dalgarno sequence. Also noted is the presence of −10 and −35 sequences upstream of the transcript initiation site, each positioned respectively at bp 124–128 and bp 101–105 in SEQ ID NO:91. A putative TodT motif is to be found at bp 30–46 in SEQ ID NO:91.

By comparing the amounts of cDNA obtained under different induction regimes, it was found that growth in the presence of toluene led to a 20-fold increase in tmoX mRNA compared to growth on citrate, with a maximal level observed 30 min after exposure to the solvent. The transcription of tmoX was also induced by the presence of p-cresol, with maximal levels also at 30 min, followed by a decrease in signal intensity probably related to exhaustion of the inducer in the culture medium.

Example 7

Regulation of pcu Expression by PCUR

The pcuC::lacZ fusion plasmid pPCUR1, and the control plasmid pPCUR2, were transformed into *Escherichia coli* MC1061. Plasmids pPCUR1 and pPCUR2 also encode PcuR and amp resistance. Cultures were grown overnight in flasks shaking at 37° C. in M9 minimal medium containing 1% glucose and 50 mg/L amp. In addition, some flasks also contained intermediate compounds of the toluene to PHBA pathway, including toluene and PHBA. The following were added at a concentration of 1 mM to separate flasks prior to overnight incubation: p-cresol, p-hydroxybenzylalcohol, p-hydroxybenzaldehyde and PHBA. Toluene (5 µL) was added to the gas phase of a 125 mL sealed flask. The overnight cultures were treated with chloroform and SDS, and assayed for β-galactosidase as described in J. H. Miller in *A Short Course in Bacterial Genetics* (Cold Spring Harbor Laboratory Press: Cold Spring Harbor, N.Y.; 1992).

Table 7 shows that when using plasmid pPCUR1 there is no induction of the pcuC::lacZ gene fusion when toluene or PHBA are present, neither of which are substrates for enzymes encoded by the pcu operon. In contrast, the presence of p-cresol, p-hydroxybenzylalcohol or p-hydroxybenzaldehyde all lead to significant induction of pcuC::lacZ, and all three compounds are substrates for the two enzymes encoded by the pcu operon i.e. PCMH and PHBAD. In the control plasmid pPCUR2, in which the pcuC gene is incorrectly orientated for expression, the presence of p-cresol does not lead to expression of β-galactosidase activity.

TABLE 7

| Plasmid | Inducer | β-galactosidase units |
|---|---|---|
| pPCUR1 | toluene | 0.55 |
| pPCUR1 | p-cresol | 19.53 |
| pPCUR2 | p-cresol | 0.05 |
| pPCUR1 | p-hydroxybenzylalcohol | 5.65 |
| pPCUR1 | p-hydroxybenzaldehyde | 9.70 |
| pPCUR1 | PHBA | 0.06 |

Example 8

Activity of Plasmid-Encoded Enzymes in *Pseudomonas putida* DOT-T1

Cells were grown in Medium A with the appropriate antibiotic in shake flasks at 30° C. (200 rpm). When the glucose had been depleted, the induction phase was initiated by addition of toluene and/or p-cresol. Three consecutive additions of inducer were made, each separated by one hour. For induction with IPTG, the compound was added at a concentration of 1 mM. Cells were collected by centrifugation, washed once with phosphate buffered saline and stored at −80° C. until assay.

TMO was measured spectrophotometrically using a coupled assay, linking phenazine ethosulfate (PES) oxidation to reduction of 2,6-dichlorophenol-indophenol (DCPIP) as measured by a decrease in absorption at 600 nm ($E_{600nm}$=21,000 $M^{-1}$ $cm^{-1}$). The assay was initiated by the addition of enzyme to a 2.0 mL reaction mixture containing 0.67 µmol PES, 0.1 µmol DCPIP, 1.0 µmol toluene and saturating levels of purified p-cresol methylhydroxylase (PCMH).

p-Cresol methylhydroxylase (PCMH) activity was measured spectrophotometrically using a coupled assay, linking phenazine ethosulfate (PES) oxidation to reduction of 2,6-dichlorophenol-indophenol (DCPIP) as measured by a decrease in absorption at 600 mn (($E_{600nm}$=21,000 $M^{-1}$ $cm^{-1}$). The assay was initiated by the addition of enzyme to a 2.0 mL reaction mixture containing 0.67 µmol PES, 0.1 µmol DCPIP and 1.0 µmol p-cresol. This assay was also used to measure toluene monooxygenase (TMO) activity by substituting 0.5–1.0 µmol toluene into the reaction mixture and by the addition of saturating levels of purified p-cresol methylhydroxylase (PCMH).

p-Hydroxybenzoate dehydrogenase (PHBAD) activity was measured spectrophoto-metrically using a reaction mix containing 600 nmol NADP+, 40 nmol p-hydroxybenzaldehyde, 1.0 mL of 50 mM glycine-NaOH (pH 9.6), and an appropriate amount of enzyme. Enzyme activity was determined by an increase in absorbance at 330 nm. A unit of activity is the amount of enzyme required to oxidize 1.0 µmol of p-hydroxybenzaldehyde per min ($E_{33\ nM}$=28,800 $M^{-1}$ $cm^{-1}$).

p-Hydroxybenzoate hydroxylase (PHBH) was assayed spectrophotometrically by following the oxidation of NADPH. The reaction mixture contained 250 nmol NADPH, 700 nmol p-hydroxybenzoate, an appropriate amounts of enzyme, and 50 mM Tris-HCl buffer (pH 8.0) to give a final volume of 1.0 mL. A unit of activity is the amount of enzyme required to oxidize 1.0 µmol of NADPH per min ($E_{340\ nm}$=6,200 $M^{-1}$ $cm^{-1}$).

Enzyme assays for PCMH and PHBAD demonstrate that both of the *Pseudomonas mendocina* pcu enzymes are expressed in *Pseudomonas putida* strain DOT-T1 (Table 8). In addition, it is noteworthy that expression of pcu is superior when using its native promoter in plasmid pMC4 compared to the use of a lac promoter in plasmid pMC3. This is also true for TMO, where greater activity is seen when using the endogenous tmo promoter in pMC4 when compared to the lac promoter in plasmid pMC3.

TABLE 8

| Plasmid | Promoter | Inducer | TMO | PCMH | PHBAD |
|---|---|---|---|---|---|
| pMC3 | lac | IPTG | 0.76 | 0.74 | |
| pMC4 | pcu or tmo | Toluene | 18.2 | 13.5 | 9.0 |
| pPCU18 | pcu | p-cresol | 0 | 16.1 | 3.6 |
| none | — | — | 0 | 0.29 | 0.05 |

Example 9

Production of PHBA from p-Cresol by *Pseudomonas putida* ATCC 29607 Transformed with a pcu Expression Plasmid The mobilizing *Escherichia coli* strain SI 7–1 was used to introduce the pcu expression plasmid pPCU12 into *Pseudomonas putida* ATCC 29607 by conjugation. A single colony of S17–1 having the plasmid pPCU12 was inoculated in 20 mL LB medium and grown at 37° C. to log phase. Another colony of *Pseudomonas putida* ATCC 29607 was inoculated in 20 mL LB medium and incubated at 30° C. and grown to log phase. The cells of both cultures were washed twice with LB medium and resuspended in LB medium. S17–1 cells harboring pPCU12 and *Pseudomonas putida* ATCC 29607 were mixed at a ratio of 1:4 and were plated on agar plates of LB medium. The plates were incubated at 30° C. for 8 h. The cells were collected and then plated on agar plates containing phosphate buffer, 1 mM succinate, 10 mM strep and 25 mg/L kan, and kan resistant colonies were selected. Transformants, or a non-transformed control strain, were grown in 15 mL M9 minimal medium containing 1% glucose, 5 mM p-cresol, 10 mM MgSO$_4$, tet (15 mg/L) in 125 mL flasks at 30° C. and 225 rpm. Samples were removed at the indicated time points and analyzed by HPLC for the presence of p-cresol and PHBA. In a plasmid-free control *Pseudomonas putida* strain failed to convert 3.3 mM p-cresol to PHBA (<0.007 mM). In contrast, *Pseudomonas putida* harboring plasmid pPCU12 produced 0.793 mM PHBA during an overnight incubation (Table 9). PHBA production is, therefore, a new attribute of *Pseudomonas putida* ATCC 29607 when transformed with and expressing pcu.

TABLE 9

| Strain | Time (h) | PHBA (mM) | p-cresol (mM) |
|---|---|---|---|
| control | 2 | <0.007 | 3.3 |
| control | 5 | <0.007 | 3.4 |
| control | 16 | <0.007 | 3.2 |
| pPCU12 | 2 | 0.141 | 2.8 |
| pPCU12 | 5 | 0.284 | 2.8 |
| pPCU12 | 16 | 0.767 | 2.2 |

Example 10

Increased Rate of Production of PHBA from p-Cresol by *Pseudomonas mendocina* Harboring a pcu Expression Plasmid Plasmid pPCU12 was transferred by conjugation from *Escherichia coli* S17–1 to *Pseudomonas mendocina* KRC16KDpobA51 as described earlier. Transformants, or a non-transformed control strain, were grown in 15 mL M9 minimal medium containing 1% glucose, 5 mM p-cresol, 10 mM MgSO$_4$, tet (15 mg/L) in 125 mL flasks at 30° C. and 225 rpm. Samples were removed at intervals of 2, 5 and 16 h and analyzed by HPLC for the presence of p-cresol and PHBA. The *Pseudomonas mendocina* KRC16KDpobA51 strain has a functional chromosomal pcu operon, but also has inactivated pobA genes to enable PHBA to accumulate. In the presence of the pPCU12 expression plasmid in *Pseudomonas mendocina* KRC16KDpobA51, PHBA accumulates more rapidly to give a concentration of 1.57 mM during the first 5 h incubation, compared to 0.526 mM for the control *Pseudomonas mendocina* strain alone (Table 10).

TABLE 10

| Strain | Time (h) | PHBA (mM) | p-cresol (mM) |
|---|---|---|---|
| control | 2 | 0.185 | 3.2 |
| control | 5 | 0.526 | 2.8 |
| control | 16 | 4.02 | 0.48 |
| pPCU12 | 2 | 0.7 | 2.8 |
| pPCU12 | 5 | 1.57 | 2.2 |
| pPCU12 | 16 | 4.84 | 0.08 |

Example 11

Production of PHBA from p-Cresol by *Agrobacterium rhizogenes* ATCC 15834 Transformed with a pcu Expression Plasmid

*Agrobacterium rhizogenes* ATCC 15834 was grown in nutrient broth at 30° C. and cells harvested during logarithmic growth. The cells were made electrocompetent by washing three times in water, centrifuging at 6000 rpm after each wash. Either the plasmid vector pGV1120 (Leemans et al., *Gene* 19:361–364 (1982)) or pMC4 were electroporated into the cells using 1 mm gap cuvettes at 1.44 kv. Cells were spread on LB plates containing 50 mg/L strep and incubated at 30° C. Transformants harboring the pGV1120 vector, or the pcu expression plasmid pMC4, were grown for 24 h in nutrient broth containing 50 mg/L strep, 10 mM MgSO$_4$, and 1 mM fully-deuterated p-cresol. PHBA was extracted from boiled cells with ether and concentrated by evaporation. Gas chromatography/mass spectrometry was used to show that the PHBA formed 0.10 (1.4 µM) contained 4 deuterium atoms. This experiment proves that it was derived from the p-cresol present during culture of the cells.

Example 12

Production of PHBA from Toluene by *Pseudomonas mendocina* Transformed with Plasmid pMC3 (pcu$^+$ tmo$^+$)

*Pseudomonas mendocina* KRC16KDpobA51 was transformed with plasmid pMC3 and selected on LB+tet (12.5 mg/L) plates at 30° C. The procedure for cell growth and toluene production was similar to that described in Example 9. The test cultures have 1 mM IPTG present at the growth and PHBA production stages in order to induce transcription from the lac promoter. No IPTG was added to the control cultures. Samples were tested for PHBA by HPLC at 1, 2, 4 and 6 h intervals. Table 11 shows that PHBA is produced by induced and non-induced cultures, but with IPTG-treated cells production started earlier, and approached levels that were within the maximum expected based on the amount of toluene added in the flasks.

TABLE 11

| | PHBA (mM) | |
|---|---|---|
| Time (h) | +IPTG | −IPTG |
| 1 | 0.147 | 0.131 |
| 2 | 0.438 | 0.180 |
| 4 | 4.985 | 1.230 |
| 6 | 7.442 | 4.172 |

Example 13

Generation of Stable ΔtodC Deficient *Pseudomonas putida* DOT-T1E Strains

*Pseudomonas putida* DOT-T1E (CECT 5312) grows on toluene via the toluene dioxygenase pathway (Mosqueda et al., *Gene* 232:69–76 (1999)). The use of this strain for PHBA production from toluene requires its inactivation. In order to generate a mutant deficient in toluene metabolism in DOT-T1E strain, a deletion of the todC1 gene in the tod operon was carried out. FIG. 5 illustrates the strategy used and the relevant constructions. The entire DOT-T1 tod operon (Mosqueda et al., *Gene* 232:69–76 (1999)) is contained in two plasmids: todXF genes borne by pT1–4, and todC1C2BADEGIHST genes borne by pT1–125. The approximately 4.5 kb EcoRI/XcaI fragment of pT1–125 which extends from todC1 to todD was cloned at the EcoRI/SmaI sites of a pUC18 Not derivative (de Lorenzo and Timmis, *Methods Enzymol.* 235:386–405 (1994)) that lacked the BamHI and HindIII at the multicopy cloning site to give plasmid pMIR17. The 1.8 kb SspI/EcoRI fragment of pT1–4 containing todXF was cloned at the EcoRI site of pMIR17 and the plasmid pMIR20 was obtained. (The unique NotI site present in the SspI/EcoRI fragment was removed before cloning). Most of the 3'-half end of todF, the entire todC1 gene, and the 5'-end of todC2 were removed from pMIR20 as a 1.6 BamHI/HindIII fragment. A 2.2 kb fragment containing the Ω/km cassette (Fellay et al., Gene 52:147–154 (1987)), encoding resistance to kanamycin, was cloned at the same position which rendered the pMIR22 plasmid. pMIR30 was obtained as the result of the subcloning in pKNG101 of the NotI fragments, which contained the region corresponding to the ΔtodC1 and the Km resistance of pMIR22. pKNG101 is a suicide vector in Pseudomonas which confers conditional lethality in the presence of sucrose (Kaniga et al., Gene 109:137–141 (1991)). pMIR30 was used to replace the todC1 gene in the chromosome of Pseudomonas putida DOT-T1E with a deleted version by homologous recombination and a toluene minus DOT-T1E derivative was obtained called .DELTA.todCkm. The absence of todC1 gene in the chromosome of the toluene minus isolate was confirmed by PCR with specific primers and in Southern blot.

55885). In this strain both pobA genes are inactivated and so it is unable to grow in p-hydroxybenzoate (WO 98/56920). Upon triparental mating with E. coli HB101 (pLAFR3:: genebank), E. coli (pRK600)—a helper strain—and Pseudomonas mendocina #303, Tc$^R$ Pseudomonas mendocina exconjugants able to grow on p-hydroxybenzoate as the sole carbon source were selected. The chimeric cosmids of these clones were isolated, their restriction pattern established and analyzed in Southern blot against the Pseudomonas mendocina pobA1 gene. A 6 kb BamHIII/EcoRI hybridization band common to all cosmids was found and cloned in pUC19 to yield pMIR18. Plasmid pMIR18 was used as the target for "artificial" in vitro random transposition, which was carried out with the Primer Island Transposition Kit (PE Applied Biosystems). A battery of plasmids carrying the AT-2 transposon at different positions was generated and E. coli DH5α cells were electroporated with the heterogeneous mix of plasmids. pobA and pobR genes were identified by sequencing from specific present at the extremes of the transposable element in pMIR27 (FIG. 6). The following primers were used:

```
1383–1399 oligo pobA1 (+) 5 GCTTCCACGGTATCTCG 3;      (SEQ ID NO:104)

1359–1343 oligo pobA1 (−) 5 CAGTCAATCCGCTGCAC 3;      (SEQ ID NO:105)

1732–1751 oligo pobA2 (+) 5 GCAGTATGGTCACCTGTTCC 3;   (SEQ ID NO:106)

1728–1710 oligo pobA2 (−) 5 GGTTCGACCACCAGGCTAC 3;    (SEQ ID NO:107)

1162–1180 oligo pobA3 (+) 5 GGATCTCAAAGCCCTGACC 3;    (SEQ ID NO:108)

963– 983 oligo pobA4 (+) 5 TGCTGCACAAGGCCGGTATCG 3;  (SEQ ID NO:109)

1945–1925 oligo pobA4 (−) 5 GGTCATGAACCAGCTGAAGCG 3;  (SEQ ID NO:110)

742– 760 oligo pobR2 (−) 5 CCTGTCCGTTAATCGAACG 3.    (SEQ ID NO:111)
```

The stability of the mutant unable to use toluene as the sole carbon-source was tested. The results can be summarized as follows: i) after 90 generations of growth on LB medium under non-selective conditions, i.e. in the absence of antibiotic markers, 100% of cells were resistant to kanamycin and unable to grow in toluene; ii) no growth was observed in M9 liquid minimal medium with toluene as the sole carbon-source; i.e. revertants were undetectable after one week in flasks with 10 mL cultures which had been inoculated with 10.sup.7 CFU/mL); iii) the reversion rate determined as the re-acquisition of the ability to grow on toluene was undetectable (lower than $10^{-9}$ by the plating technique).

Example 14

Cloning of the Pseudomonas putida pobA Gene

The pobA gene encodes the enzyme para-hydoxybenzoate hydroxylase and converts PHBA into protocarechuate. Production of PHBA requires that its metabolism through the pobA pathway be impaired. To this end, pobA was first cloned, then it was inactivated it in vitro and the mutation transferred to the chromosome of ΔtodKm. To clone Pseudomonas putida pobA gene, a Pseudomonas putida KT2440 (ATCC 47054) built in the tetracycline (Tc)-resistant pLAFR3 cosmid (Rodriguez-Herva et al., J. Bacteriol. 178:1699–1706 (1996)) was used for the complementation of the Pseudomonas mendocina KRC16KDpobA51 (ATCC Example 15

Generation of p-Hydroxybenzoate Minus Derivative of Pseudomonas putida T1-E ΔtodCkm To knock-out the pobA gene in the chromosome of the toluene minus Pseudomonas putida ΔtodCkm strain, plasmid pMIR31 was generated with a pobA inactivated copy (FIG. 6). Plasmid pMIR31 bore Pseudomonas putida KT2440 pobA gene interrupted by the interposon Ω/Sm. This chimeric plasmid is a suicide vector in Pseudomonas and was used as a delivery system for gene replacement of the wild type pobA allele for an inactivated copy by homologous recombination.

Pseudomonas putida ΔtodCkm cells were electroporated with pMIR31 and after high voltage pulse, cells were incubated in SOC medium for two h at 30° C., then centrifuged and the pellet incubated overnight on an LB-agar plate. Finally, Sm-resistant transconjugants were selected on LB plates with Km, 25 μg/mL, and Sm, 150 μg/mL. This selection medium permitted the growth of the clones resulting from a single cointegration event of pMIR31 in the host chromosome, as well as an eventually successful gene replacement after the resolution of the cointegrate. Two hundred Km$^r$ Sm$^r$ colonies were tested for their ability to grow on p-hydroxybenzoate as the sole carbon source and for piperacillin resistance (Pip$^r$)—the marker of the pMIR31 plasmid that allowed one to confirm the cointegration of the host chromosome of confirm the successful allelic exchange of the wild-type pobA gene for the inactivated copy confirmed by Southern blot. The double mutant was called *Pseudomonas putida* todCKmpobA::Sm.

Example 16

Recruitment of *Pseudomonas mendocina* KR1 Toluene Monooxygenase/p-Cresol

Utilization Pathways in *Pseudomonas putida* ΔtodCKmpobA::Sm (Construction of a miniTn5Tctmo/pcu Transposon and Production of PHBA)

A transposon was constructed based on a miniTn5Tc with *Pseudomonas mendocina* tmo/pcu genes which permitted integrating these catabolic genes in the chromosome of the double mutant *Pseudomonas putida* ΔtodCKmpobA::Sm and so produced p-hydroxybenzoate from toluene. The scheme of the construction of the transposon is shown in FIG. 7. The 7.5 kb BamHI fragment of pMC4 containing the tmoXABCDEF genes was subloned at the same site in the polylinker of pUC19, generating the plamid pMIR32. The 7.6 MluI/NheI fragment of pPCU17 containing the pcuR-CAB genes was subcloned at the HindII/XbaI sites of pUC18NotI. In the plasmid so generated, pMIR40, the 7.4 kb BamHI fragment of pMIR32 containing the tmo operon was cloned at the BamHI site.

Then the 15 kb NotI fragment containing pcu and tmo genes was cloned at the unique NotI site of pUT/Tc (de Lorenzo and Timmis, *Methods Enzymol.* 235:386–405 (1994)) generating the plasmid pMIR44 (the unique NotI site of pUT/Tc is located within the transposable element miniTn5Tc born by the plasmid pUT which is suicide in *Pseudomonas*). The transposon was delivered in the chromosome of the double mutant *Pseudomonas putida* ΔtodCKmpobA::Sm via a triparental mating with CC118λpir (pMIR44) as a donor and HB101 (pRK600) as a helper strain. Exconjugants Km$^r$ Sm$^r$ Tc$^r$ were selected with a rate of 5×10$^{-8}$. The presence of the miniTn5Tctmo/pcu transposon was confirmed in the Tc$^r$ exconjugants by PCR-amplification of the tmoA gene. This strain produces more than 2 g/L PHBA when grown with glucose in the presence of toluene.

Example 17

Construction of a pobA Mutant of *Pseudomonas putida* KT2440 and Recruitment of miniTn5Tctmo/pcu Plasmid pMIR31 was also used to replace the wild-type pobA gene of *Pseudomonas putida* KT2440 with a mutant allele as it was carried out with *Pseudomonas putida* ΔtodCKm. The resolution of the merodiploid colonies was tested for Sm resistance and Pip sensitivity. One out of 100 colonies exhibited this character and was unable to grow on p-hydroxybenzoate as the sole carbon source. The allelic exchange was further confirmed on Southern blot.

The catabolic genes tmo/pcu were recruited in *Pseudomonas putida* pobA through a triparental mating with CC118λpir (pMIR44), HB101 (pRK600) and *Pseudomonas putida* pobA, as it was previously conducted for the recruitment of the miniTn5Tctmo/pcu in *Pseudomonas putida* ΔtodCKmpobA::Sm. Nevertheless, this strain only produced trace amounts of PHBA. However production of PHBA was achieved when the regulatory todST genes of *Pseudomonas putida* DOT-T1E (SEQ ID NO:112; GenBank Accession Number Y18245; Mosqueda et al., *Gene* 232:69–76 (1999)) were introduced in the strain after subcloning in plasmid pBBR1-MCS5. This strain produced PHBA up to 10–15 mM in 250 mL flasks with 3 mL culture containing about 10$^8$ cells/mL and incubated at 30° C. on an orbital platform operated at 200 strokes per min. This example indicates that the regulatory genes of the tod pathway induce the tmo pathway.

The heterologous TodST proteins that control the induction of toluene dioxygenase pathway, are able to induce high levels of expression from the tmo pathway genes, and are useful tools to mediate expression of the catabolic tmo genes and PHBA production in any organism that does not possess these genes. Previously, Lau and co-workers (*Proc. Natl. Acad. Sci.* USA 94:1453–1458 (1997)) have shown that the two regulatory genes from *Pseudomonas putida* F1, todS and todT, are members of a two-component signal transduction family of bacteria uses a histidine-asparate phosphorelay circuit to sense environmental changes. The genes in the instant invention are 95–100% homologous to the tod genes in *Pseudomonas putida* F1.

What is claimed is:

1. A method for the production of p-hydroxybenzoate (PHBA) comprising:
   (i) contacting a transformed bacterial host cell with a medium containing
      (a) an aromatic organic substrate selected from the group consisting of p-cresol, p-hydroxybenzyl alcohol, p-hydroxybenzaldehyde, and aromatic compounds degradated by the toluene monooxygenase enzyme pathway,
      (b) at least one fermentable carbon substrate, and
      (c) a nitrogen source, the transformed bacterial host cell 1) lacking a p-hydroxybenzoate hydroxylase activity and 2) comprising genes encoding PcuR, p-cresol methylhydroxylase, and p-hydroxybenzoate dehydrogenase activities, each gene operably linked to suitable regulatory sequences;
   (ii) incubating the transformed bacterial host cell for a time sufficient to produce PHBA; and
   (iii) optionally recovering the p-hydroxybenzoate produced in (ii).

2. The method of claim 1 wherein the aromatic organic substrate is p-cresol.

3. The method of claim 1 wherein the fermentable carbon substrate is selected from the group consisting of monosaccharides, oligosaccharides, polysaccharides, carbon dioxide, methanol, formaldehyde, formate, and carbon-containing amines.

4. The method of claim 3 wherein the fermentable carbon substrate is glucose.

5. The method of claim 1 wherein the transformed bacterial host cell is selected from the group consisting of Pseudomonas, Burkholderia, Acinetobacter, and Agrobacterium.

6. The method of claim 2 wherein p-cresol is present in the medium in a concentration of less than 500 ppm.

7. The method of claim 2 wherein p-cresol is present in the medium from about 30 ppm to about 60 ppm.

* * * * *

SEQUENCE LISTING

<160> NUMBER OF SEQ ID NOS: 112

<210> SEQ ID NO 1
<211> LENGTH: 6491
<212> TYPE: DNA
<213> ORGANISM: Pseudomonas mendocina KR-1

<400> SEQUENCE: 1

```
tcactccccc ttgagccggt agctgatctg cgcgcgactc atgcccaaca tctgcgccgc      60
cgcggtgagg ttgccgccgg tgcgttccag ggcaaggtgc accaggcgct gctcgatctc     120
cttcagtgat gtgcctagta cccggtcgcg cccggcgagg aaggcctgca ggttggccag     180
ccccagctca accggttcat gctcctcgac aaccacctca gcccgcgctt gcggttcgcc     240
gccgacggca tccagacggc cttcggcggt caggccgatg ccgctggagc gaagtggctc     300
```

-continued

```
gccggctttt gccaggtgca ccaggtcgat cagctcgcca ctgcctgcgg cgatcacgcc      360
gcgctcgatc aggttctgca gctcacggat attgccgggg aagcgtagg tcagcagcgc       420 gttgaccagc cgcgtgctga aacccagggg tttgagccca tggcgcgcac tgaacttgcg      480
caggaagtag ctcatcagga gcgggatgtc ctcacgcgcg tcgcgcaggg gcggcagatg      540 gatgggaac acgttcagcc ggtacagcag gtcctcgcgg aagcgccggg cctcgacctc       600
tcggcgcagg tccagattgg tggcggcgat caccctcaca tccaccggga tcgccgaggt      660
accacctacc cgctcgatct cgccctcctg cagcacccgc aggatcttgc tctgggcgct      720
gaggctcagg gtggcgatct cgtcgaggaa cagggtgccg cccttggccc gctcgaagcg      780
ccccgggcgg gaacggtcgg cgccggtgaa ggcaccgcgc tccacgccga acagttcggc      840
ttccagcaga gtttccggca acgccgcgca gttgagcgcc accaacgcg tttggcggcg       900 cgggctggcc tggtgcaggg tgcgcgcgaa gagctccttg cccacccccg attcaccggt      960
cagcagtacg gtgcctggg tcgacgcaac gcggtagagc tgctggctgg cggcgacaaa      1020
ggcggcggaa atgcccacca tggcctggtc ctcgggcggc tcatccagat cggccatttc     1080
cgtctcgtct gccgagccgt aggtgctccg gctgaggaag tcgctggcat ccaggtgggc     1140
caggtcggtg tcgatgtcct cccactgctc cgccggcttg ccgacgatgc ggcacgccga     1200
atggcccatg cagcggcatt cctgctcgcg gaacaccacc aggcgcccca gcagggagga     1260
ggtgtagccg ctggcgtagc ccacttccat ccagcaggcc ggttcgctgc ccagcccgta     1320
gctggcgatg tgctcgtcgg cttccaggga gttgtgccag aagaattcgg aatagaaatg     1380
cccgatgctg gagtcgatgt cgaagcgcac cacttccacg ttcaccatgc cctccagcat     1440
gtgcaggcgc gggcctgcgc tgtagaggct ggcgtggtcg ccctcgggcc actgcgcgct     1500
gacctgagcg gcatccctcg ttccggcctg ccagccaatg cgggtcagaa ggccacgggc     1560
cttgtcgagg ccgagggctt ccaccaactc gcgacggatg gcgccgaagg cggccccctg     1620
cagcagcatc atgcgctggc cgcagagcca gatattgcca tcctggggcg cgaaggcgac     1680
ggtctccgcc agttgctcgg ccgagggcag cccgctgctg ccgaactggt tggcctggtc     1740
gacgatcagg ctcttctgcc ggccgagcaa ctgcttgagg aattcatccc ccatgctgcg     1800
gccgggattg ctcgagggtt tgcgagtcat ggtcatgggg cgggaggtag gaacaatgtt     1860
attcagtatg cccgtgtgaa atggccggtc aattggccct tgccatcacc caataatcgc     1920
ccaacctctt gcagaccact ccggagaagt ttctgcgccc cggagacttc tctgaagaaa     1980
aatcggcgcc aaccctcccg caagcccccc atgcgtccgc tccgcattcc ccaaaaaaac     2040
gtaaccaatt gttttacaaa taaaaaatag aagaagaag gattggcacg gtagttgtta     2100
aaggacaggg gcgtgcaccc aagacaataa caacacaggt aacgaccta tgaaccgctt     2160 cccatcgcca atccattccg cttgcccacc cgcaccacgg cttcgttgtt gaccctcaac     2220
cgtacctcca caggaacggc gcccgcgcgt cttgcctgac gtatcgccac cgcccgtgt     2280 aaccaccggc tcgccgccac tggcagcctt ccgcgcaaac aagagagaac ccatggacac     2340
cacccgccct gcctaccaga acctcgagct ccaacctctc gccgggcaat ggcgcgccgg     2400
cagtagcggt cgcccgttgg aggtcttcga cccctacaac gacgagctgc tattgcgcat     2460
cgccctggcc agccgcgaag acctcgacg agcctaccgc aaggcccgcg acagccagcg     2520
ggagtgggcg accacggcgc cggccgagcg cgcccgggtg ctgctggaag cggtgaagat     2580
cttcgatgag cgccgcgagg agattatcga ctggatcatc cgcgagtccg gcagcacccg     2640
catcaaggcg cagatcgaat ggggcgccgc ccgcgccatc accctggagt cggccagcct     2700
```

-continued

```
gccgaatcgc gtgcacgggc gcatcatcgc ctccaacatc tccggcaagg agagccgcgt      2760
gtaccgcgcg cccctgggcg tgatcggcgt gatcagtccg tggaacttcc ccctgcacct      2820
cactgcccgc tccctggccc cggccctggc cctgggcaat gccgtggtgg tcaagccggc      2880
cagcgacacc ccgatcaccg gtggcctact gctggcgcgc atcttcgaag aagccggcct      2940
gccggcgggg gtgctcagcg tggtggtggg ttcgggcgcg gagattggtg acgccttcgt      3000
cgagcacccg gtgcccgccc tcatttcctt caccggctcc actcaggtgg gccgcaacat      3060
cggccgcatc gccagcggcg gtgagcacct caagcacgtg gcgctggaac tgggcggcaa      3120
cagcccgttt gtggtcttgg ccgatgccga cgtggagcag gcggtgaatg cggccgtggt      3180
cggcaagttc ctgcaccagg gccagatctg catggcgatc aaccgcatta tcgtcgagca      3240
gcctttgctg gaagatttca cccgccgctt cgtcgagcgc gtcaaggccc tgccctatgg      3300
cgacccgagc aagccgggga ccgtggtcgg tccggtgatc aacgccaggc agctggccgg      3360
tctgaaggag aagatcgcca ccgccaaggc cgaaggcgcc accctgctgc tgggtggcga      3420
gccccagggc aacgtcatgc cgccccatgt gttcggcaac gtcaccgccg acatggaaat      3480
cgcccgcgaa gaaattttcg gcccgctggt gggcatccaa tccgcccgtg acgccgaaca      3540
cgccctggag ttggccaaca gcagcgagta cggcctgtcc agcgcggtgt tcaccgccag      3600
cctcgagcgc ggcgtgcagt tcgcccggcg catccacgcc ggcatgaccc acgtgaacga      3660
catcccggtt aacgacgagc caacgctcc cttcggcggc gagaagaact ctggcctcgg      3720
ccgcttcaac ggcgactggg ccatcgagga gttcaccacc gatcactgga tcaccctgca      3780
acacagcccg cggccctatc cgttctgatg ctgccgcatc cccatcaccc agccccaata      3840
aaaaacggag tacgaaatgt cctcactcct caacagccga gctgtgaaac ggccactgct      3900
ggccagcctt gcactaattt tcgccctgct cgccggccag gccttcgccg acggcgacgg      3960
cgtctggaaa ggcggcgaga acgtctacca gaaaatctgt ggccactgcc acgaaaaaca      4020
ggtgggcccg gtgatcaccg gccgccagct accgccgcag tacatcagtg ccgtggtgcg      4080
caacggcttc cgcgccatgc cggccttttcc ggcctcgttc atcgacgaca aggccctgca      4140
gcaggtcgcc gagtacatct ccaagacccc tgctactgtg gccaagccct gaggtgccgg      4200
cgatgaacat cgaacgtcgt accctgctca agggcatggc cctgggcggc ctggctggcg      4260
ccgccatggg cgccttcggc ctggcgatga ccaaggccat gctgggcggg caggcccagc      4320
cactgcccac cctcgtcctg gtagatggcg aggcggccgg agcggccttc ctcgccggag      4380
tcggttccag cccggcggcc agcaaggccg aggtgcagcg caccgatctc ggcctggact      4440
tcgtcttggg cctggagaag cgcctgcgca gtggtcagca gcaacgcatc atcggtctgg      4500
tggatgacgc cagcgccgct ctgatcctcg acctggcccg cagcagcggc gcgcgggtgc      4560
agtggctcgg ccagcatagc gccgcggccg gctcctcccg gcaccgtctg ctcagcgccg      4620
acagcgccca gggctgctcc cttcgcctgg gccagcagct ccatgcctgc ggcggcggct      4680
tcagcctgag cgaacagcac cccctgggtg ccagcccct gaatctggcc ggtgccgcgc      4740
gcagcggcgg ctccgcgcaa tgggcggcca gcatcggcca cgacctggcc agcctgggcg      4800
gcgatgacag cagtgcggcc ccacgcattg ccaaccatta cccggcgctt accggccaat      4860
tcgtttcgtt ctcgatcctg gtttgaagga gctgacagat gaccgagcaa acccagaaca      4920
ccctgattcc ccgtggcgtg aatgacgcca acctccagca agcccctggcc aagttccgca      4980 agctgctggg cgaggacaac gtcctggtca aggacgagca actcatcccc tacaacaaga      5040
```

-continued

```
tcatgatcgc agtggacaac gccgaacacg cgccctccgc tgctgtcacc gccaccactg    5100
tggaacaggt gcaggcgtg gtgaagatct gcaacgaata cggcattccg gtgtggacca    5160
tctccaccgg ccgcaacttc ggttacggct cggcggcccc cggccagcgt ggccaggtga    5220
tcctcgacct gaagaaaatg aacaagatca tccacgtaga cccggacctg tgcaccgccc    5280
tggtggaacc gggggtgacc taccagcagc tgtacgatta cctggaagag aacaacatcc    5340
cgctgatgct gtccttctct gcaccctcgg ccatcgccgg ccgctgggc aacaccatgg    5400
accgtggcgt gggctacacc ccctacggcg agcacttcct catgcagtgc ggcatggaag    5460
tggtgctggc caatggcgac gtctaccgca ccggcatggg cggggtgaaa ggcgacaacg    5520
cctggcaggt gttcaagtgg ggctacggcc cgaccctgga cggcatgttc acccaggcca    5580
actacggcat ctgcaccaag atgggtttct ggctgatgcc caagcccccg gtgttcaagc    5640
ccttcgagat caagttcgag aacgagtccg acatcagcga gatcgtcgaa ttcatccgtc    5700
cgctgcgcat cgcccaggtc atcccaaact ccgtggtgat cgccggtgtg ctctgggagg    5760
cctccacctg caatacccgc cgctcggact acaccactga gccgggcgcc actcccgaca    5820
ccatcctgaa gcagatccag aaggacaagg aactcggcgc ctggaacgtc tatgccgctc    5880
tctacggcac gcaggaacag gtggacgtga actggaagat cgtcaccggc gccctggcca    5940
aactgggcaa gggcaggatt gtcacccagg aagaggccgg cgatacccag cccttcaagt    6000
accgttccca gttgatgtcc ggcgtcccca acctgcagga attcggcctg tacaactggc    6060
gcggggggcgg cggctccatg tggttcgccc cggtcagcca ggcccgtggc atcgagtgcg    6120
acaagcagca ggcgctggcc aagaagatcc tcaacaagca cggcctggac tacgtcggcg    6180
agttcattgt cggctggcgc gacatgcacc acgtaatcga cgtgctgtac gaccgcacca    6240
accccgagga aacccaacgc gcctacgcct gcttccacga gttgctggat gagttcgaga    6300
agcacggcta tgcggtgtac cgcgtgaaca ctgcgttcca ggagcgcgtg gcgcagaggt    6360
acggcacggt caagcgcagg tggaacacgc catcaagcgc gccctggacc cgaacaacat    6420
cctggcaccc ggcaaatccg gcatcgacct cgccaacaag ttctaaccct aagcaagacc    6480
ccgccgggta a                                                         6491
```

<210> SEQ ID NO 2
<211> LENGTH: 611
<212> TYPE: PRT
<213> ORGANISM: Pseudomonas mendocina KR-1

<400> SEQUENCE: 2

```
Met Thr Met Thr Arg Lys Pro Ser Ser Asn Pro Gly Arg Ser Met Gly
  1               5                  10                  15

Asp Glu Phe Leu Lys Gln Leu Leu Gly Arg Gln Lys Ser Leu Ile Val
             20                  25                  30

Asp Gln Ala Asn Gln Phe Gly Ser Ser Gly Leu Pro Ser Ala Glu Gln
         35                  40                  45

Leu Ala Glu Thr Val Ala Phe Ala Pro Gln Asp Gly Asn Ile Trp Leu
     50                  55                  60

Cys Gly Gln Arg Met Met Leu Leu Gln Gly Ala Ala Phe Gly Ala Ile
 65                  70                  75                  80

Arg Arg Glu Leu Val Glu Ala Leu Gly Leu Asp Lys Ala Arg Gly Leu
                 85                  90                  95

Leu Thr Arg Ile Gly Trp Gln Ala Gly Thr Arg Asp Ala Ala Gln Val
            100                 105                 110
```

-continued

```
Ser Ala Gln Trp Pro Glu Gly Asp His Ala Ser Leu Tyr Ser Ala Gly
            115                 120                 125

Pro Arg Leu His Met Leu Glu Gly Met Val Asn Val Glu Val Val Arg
130                 135                 140

Phe Asp Ile Asp Ser Ser Ile Gly His Phe Tyr Ser Glu Phe Phe Trp
145                 150                 155                 160

His Asn Ser Leu Glu Ala Asp Glu His Ile Ala Ser Tyr Gly Leu Gly
            165                 170                 175

Ser Glu Pro Ala Cys Trp Met Glu Val Gly Tyr Ala Ser Gly Tyr Thr
            180                 185                 190

Ser Ser Leu Leu Gly Arg Leu Val Phe Arg Glu Gln Glu Cys Arg
            195                 200                 205

Cys Met Gly His Ser Ala Cys Arg Ile Val Gly Lys Pro Ala Glu Gln
            210                 215                 220

Trp Glu Asp Ile Asp Thr Asp Leu Ala His Leu Asp Ala Ser Asp Phe
225                 230                 235                 240

Leu Ser Arg Ser Thr Tyr Gly Ser Ala Asp Glu Thr Glu Met Ala Asp
            245                 250                 255

Leu Asp Glu Pro Pro Glu Asp Gln Ala Met Val Gly Ile Ser Ala Ala
            260                 265                 270

Phe Val Ala Ala Ser Gln Gln Leu Tyr Arg Val Ala Ser Thr Gln Ala
            275                 280                 285

Thr Val Leu Leu Thr Gly Glu Ser Gly Val Gly Lys Glu Leu Phe Ala
            290                 295                 300

Arg Thr Leu His Gln Ala Ser Pro Arg Arg Gln Thr Pro Leu Val Ala
305                 310                 315                 320

Leu Asn Cys Ala Ala Leu Pro Glu Thr Leu Leu Glu Ala Glu Leu Phe
            325                 330                 335

Gly Val Glu Arg Gly Ala Phe Thr Gly Ala Asp Arg Ser Arg Pro Gly
            340                 345                 350

Arg Phe Glu Arg Ala Lys Gly Gly Thr Leu Phe Leu Asp Glu Ile Ala
            355                 360                 365

Thr Leu Ser Leu Ser Ala Gln Ser Lys Ile Leu Arg Val Leu Gln Glu
            370                 375                 380

Gly Glu Ile Glu Arg Val Gly Gly Thr Ser Ala Ile Pro Val Asp Val
385                 390                 395                 400

Arg Val Ile Ala Ala Thr Asn Leu Asp Leu Arg Arg Glu Val Glu Ala
            405                 410                 415

Gly Arg Phe Arg Glu Asp Leu Leu Tyr Arg Leu Asn Val Phe Pro Ile
            420                 425                 430

His Leu Pro Pro Leu Arg Glu Arg Arg Glu Asp Ile Pro Leu Leu Met
            435                 440                 445

Ser Tyr Phe Leu Arg Lys Phe Ser Ala Arg His Gly Leu Lys Pro Leu
            450                 455                 460

Gly Phe Ser Thr Arg Leu Val Asn Ala Leu Leu Thr Tyr Arg Phe Pro
465                 470                 475                 480

Gly Asn Ile Arg Glu Leu Gln Asn Leu Ile Glu Arg Gly Val Ile Ala
            485                 490                 495

Ala Gly Ser Gly Glu Leu Ile Asp Leu Val His Leu Ala Lys Ala Gly
            500                 505                 510

Glu Pro Leu Arg Ser Ser Gly Ile Gly Leu Thr Ala Glu Gly Arg Leu
            515                 520                 525

Asp Ala Val Gly Gly Glu Pro Gln Ala Arg Ala Glu Val Val Val Glu
```

530                 535                 540
Glu His Glu Pro Val Glu Leu Gly Leu Ala Asn Leu Gln Ala Phe Leu
545                 550                 555                 560

Ala Gly Arg Asp Arg Val Leu Gly Thr Ser Leu Lys Glu Ile Glu Gln
                565                 570                 575

Arg Leu Val His Leu Ala Leu Glu Arg Thr Gly Gly Asn Leu Thr Ala
            580                 585                 590

Ala Ala Gln Met Leu Gly Met Ser Arg Ala Gln Ile Ser Tyr Arg Leu
        595                 600                 605

Lys Gly Glu
    610

<210> SEQ ID NO 3
<211> LENGTH: 491
<212> TYPE: PRT
<213> ORGANISM: Pseudomonas mendocina KR-1

<400> SEQUENCE: 3

Met Asp Thr Thr Arg Pro Ala Tyr Gln Asn Leu Glu Leu Gln Pro Leu
1               5                   10                  15

Ala Gly Gln Trp Arg Ala Gly Ser Ser Gly Arg Pro Leu Glu Val Phe
            20                  25                  30

Asp Pro Tyr Asn Asp Glu Leu Leu Arg Ile Ala Leu Ala Ser Arg
        35                  40                  45

Glu Asp Leu Asp Ala Ala Tyr Arg Lys Ala Arg Asp Ser Gln Arg Glu
    50                  55                  60

Trp Ala Thr Thr Ala Pro Ala Glu Arg Ala Arg Val Leu Leu Glu Ala
65                  70                  75                  80

Val Lys Ile Phe Asp Glu Arg Glu Glu Ile Ile Asp Trp Ile Ile
                85                  90                  95

Arg Glu Ser Gly Ser Thr Arg Ile Lys Ala Gln Ile Glu Trp Gly Ala
            100                 105                 110

Ala Arg Ala Ile Thr Leu Glu Ser Ala Ser Leu Pro Asn Arg Val His
        115                 120                 125

Gly Arg Ile Ile Ala Ser Asn Ile Ser Gly Lys Glu Ser Arg Val Tyr
    130                 135                 140

Arg Ala Pro Leu Gly Val Ile Gly Val Ile Ser Pro Trp Asn Phe Pro
145                 150                 155                 160

Leu His Leu Thr Ala Arg Ser Leu Ala Pro Ala Leu Ala Leu Gly Asn
                165                 170                 175

Ala Val Val Lys Pro Ala Ser Asp Thr Pro Ile Thr Gly Gly Leu
            180                 185                 190

Leu Leu Ala Arg Ile Phe Glu Glu Ala Gly Leu Pro Ala Gly Val Leu
        195                 200                 205

Ser Val Val Gly Ser Gly Ala Glu Ile Gly Asp Ala Phe Val Glu
    210                 215                 220

His Pro Val Pro Ala Leu Ile Ser Phe Thr Gly Ser Thr Gln Val Gly
225                 230                 235                 240

Arg Asn Ile Gly Arg Ile Ala Ser Gly Gly Glu His Leu Lys His Val
                245                 250                 255

Ala Leu Glu Leu Gly Gly Asn Ser Pro Phe Val Val Leu Ala Asp Ala
            260                 265                 270

Asp Val Glu Gln Ala Val Asn Ala Ala Val Val Gly Lys Phe Leu His
        275                 280                 285

```
Gln Gly Gln Ile Cys Met Ala Ile Asn Arg Ile Ile Val Glu Gln Pro
    290                 295                 300

Leu Leu Glu Asp Phe Thr Arg Arg Phe Val Glu Arg Val Lys Ala Leu
305                 310                 315                 320

Pro Tyr Gly Asp Pro Ser Lys Pro Gly Thr Val Val Gly Pro Val Ile
                325                 330                 335

Asn Ala Arg Gln Leu Ala Gly Leu Lys Glu Lys Ile Ala Thr Ala Lys
                340                 345                 350

Ala Glu Gly Ala Thr Leu Leu Gly Gly Glu Pro Gln Gly Asn Val
                355                 360                 365

Met Pro Pro His Val Phe Gly Asn Val Thr Ala Asp Met Glu Ile Ala
    370                 375                 380

Arg Glu Glu Ile Phe Gly Pro Leu Val Gly Ile Gln Ser Ala Arg Asp
385                 390                 395                 400

Ala Glu His Ala Leu Glu Leu Ala Asn Ser Ser Glu Tyr Gly Leu Ser
                405                 410                 415

Ser Ala Val Phe Thr Ala Ser Leu Glu Arg Gly Val Gln Phe Ala Arg
                420                 425                 430

Arg Ile His Ala Gly Met Thr His Val Asn Asp Ile Pro Val Asn Asp
                435                 440                 445

Glu Pro Asn Ala Pro Phe Gly Gly Lys Asn Ser Gly Leu Gly Arg
450                 455                 460

Phe Asn Gly Asp Trp Ala Ile Glu Glu Phe Thr Thr Asp His Trp Ile
465                 470                 475                 480

Thr Leu Gln His Ser Pro Arg Pro Tyr Pro Phe
                485                 490

<210> SEQ ID NO 4
<211> LENGTH: 111
<212> TYPE: PRT
<213> ORGANISM: Pseudomonas mendocina KR-1

<400> SEQUENCE: 4

Met Ser Ser Leu Leu Asn Ser Arg Ala Val Lys Arg Pro Leu Leu Ala
  1               5                  10                  15

Ser Leu Ala Leu Ile Phe Ala Leu Leu Ala Gly Gln Ala Phe Ala Asp
                 20                  25                  30

Gly Asp Gly Val Trp Lys Gly Gly Glu Asn Val Tyr Gln Lys Ile Cys
             35                  40                  45

Gly His Cys His Glu Lys Gln Val Gly Pro Val Ile Thr Gly Arg Gln
         50                  55                  60

Leu Pro Pro Gln Tyr Ile Ser Ala Val Val Arg Asn Gly Phe Arg Ala
 65                  70                  75                  80

Met Pro Ala Phe Pro Ala Ser Phe Ile Asp Asp Lys Ala Leu Gln Gln
                 85                  90                  95

Val Ala Glu Tyr Ile Ser Lys Thr Pro Ala Thr Val Ala Lys Pro
                100                 105                 110

<210> SEQ ID NO 5
<211> LENGTH: 227
<212> TYPE: PRT
<213> ORGANISM: Pseudomonas mendocina KR-1

<400> SEQUENCE: 5

Met Asn Ile Glu Arg Arg Thr Leu Leu Lys Gly Met Ala Leu Gly Gly
  1               5                  10                  15
```

-continued

```
Leu Ala Gly Ala Ala Met Gly Ala Phe Gly Leu Ala Met Thr Lys Ala
            20                  25                  30

Met Leu Gly Gly Gln Ala Gln Pro Leu Pro Thr Leu Val Leu Val Asp
        35                  40                  45

Gly Glu Ala Ala Gly Ala Ala Phe Leu Ala Gly Val Gly Ser Ser Pro
    50                  55                  60

Ala Ala Ser Lys Ala Glu Val Gln Arg Thr Asp Leu Gly Leu Asp Phe
65                  70                  75                  80

Val Leu Gly Leu Glu Lys Arg Leu Arg Ser Gly Gln Gln Gln Arg Ile
                85                  90                  95

Ile Gly Leu Val Asp Asp Ala Ser Ala Leu Ile Leu Asp Leu Leu Ala
            100                 105                 110

Arg Ser Ser Gly Ala Arg Val Gln Trp Leu Gly Gln His Ser Ala Ala
        115                 120                 125

Ala Gly Ser Ser Arg His Arg Leu Leu Ser Ala Asp Ser Ala Gln Gly
    130                 135                 140

Cys Ser Leu Arg Leu Gly Gln Gln Leu His Ala Cys Gly Gly Gly Phe
145                 150                 155                 160

Ser Leu Ser Glu Gln His Pro Leu Gly Gly Pro Leu Asn Leu Ala
                165                 170                 175

Gly Ala Ala Arg Ser Gly Gly Ser Ala Gln Trp Ala Ala Ser Ile Gly
            180                 185                 190

His Asp Leu Ala Ser Leu Gly Gly Asp Asp Ser Ser Ala Ala Pro Arg
        195                 200                 205

Ile Ala Asn His Tyr Pro Ala Leu Thr Gly Gln Phe Val Ser Phe Ser
    210                 215                 220

Ile Leu Val
225

<210> SEQ ID NO 6
<211> LENGTH: 530
<212> TYPE: PRT
<213> ORGANISM: Pseudomonas mendocina KR-1

<400> SEQUENCE: 6

Met Thr Glu Gln Thr Gln Asn Thr Leu Ile Pro Arg Gly Val Asn Asp
1               5                   10                  15

Ala Asn Leu Gln Gln Ala Leu Ala Lys Phe Arg Lys Leu Leu Gly Glu
            20                  25                  30

Asp Asn Val Leu Val Lys Asp Glu Gln Leu Ile Pro Tyr Asn Lys Ile
        35                  40                  45

Met Ile Ala Val Asp Asn Ala Glu His Ala Pro Ser Ala Ala Val Thr
    50                  55                  60

Ala Thr Thr Val Glu Gln Val Gln Gly Val Val Lys Ile Cys Asn Glu
65                  70                  75                  80

Tyr Gly Ile Pro Val Trp Thr Ile Ser Thr Gly Arg Asn Phe Gly Tyr
                85                  90                  95

Gly Ser Ala Ala Pro Gly Gln Arg Gly Gln Val Ile Leu Asp Leu Lys
            100                 105                 110

Lys Met Asn Lys Ile Ile His Val Asp Pro Asp Leu Cys Thr Ala Leu
        115                 120                 125

Val Glu Pro Gly Val Thr Tyr Gln Gln Leu Tyr Asp Tyr Leu Glu Glu
    130                 135                 140

Asn Asn Ile Pro Leu Met Leu Ser Phe Ser Ala Pro Ser Ala Ile Ala
145                 150                 155                 160
```

```
Gly Pro Leu Gly Asn Thr Met Asp Arg Gly Val Gly Tyr Thr Pro Tyr
            165                 170                 175
Gly Glu His Phe Leu Met Gln Cys Gly Met Glu Val Val Leu Ala Asn
            180                 185                 190
Gly Asp Val Tyr Arg Thr Gly Met Gly Val Lys Gly Asp Asn Ala
            195                 200                 205
Trp Gln Val Phe Lys Trp Gly Tyr Gly Pro Thr Leu Asp Gly Met Phe
    210                 215                 220
Thr Gln Ala Asn Tyr Gly Ile Cys Thr Lys Met Gly Phe Trp Leu Met
225                 230                 235                 240
Pro Lys Pro Pro Val Phe Lys Pro Phe Glu Ile Lys Phe Glu Asn Glu
                245                 250                 255
Ser Asp Ile Ser Glu Ile Val Glu Phe Ile Arg Pro Leu Arg Ile Ala
            260                 265                 270
Gln Val Ile Pro Asn Ser Val Val Ile Ala Gly Val Leu Trp Glu Ala
        275                 280                 285
Ser Thr Cys Asn Thr Arg Arg Ser Asp Tyr Thr Thr Glu Pro Gly Ala
    290                 295                 300
Thr Pro Asp Thr Ile Leu Lys Gln Ile Gln Lys Asp Lys Glu Leu Gly
305                 310                 315                 320
Ala Trp Asn Val Tyr Ala Ala Leu Tyr Gly Thr Gln Glu Gln Val Asp
                325                 330                 335
Val Asn Trp Lys Ile Val Thr Gly Ala Leu Ala Lys Leu Gly Lys Gly
            340                 345                 350
Arg Ile Val Thr Gln Glu Glu Ala Gly Asp Thr Gln Pro Phe Lys Tyr
        355                 360                 365
Arg Ser Gln Leu Met Ser Gly Val Pro Asn Leu Gln Glu Phe Gly Leu
    370                 375                 380
Tyr Asn Trp Arg Gly Gly Gly Ser Met Trp Phe Ala Pro Val Ser
385                 390                 395                 400
Gln Ala Arg Gly Ile Glu Cys Asp Lys Gln Gln Ala Leu Ala Lys Lys
                405                 410                 415
Ile Leu Asn Lys His Gly Leu Asp Tyr Val Gly Glu Phe Ile Val Gly
            420                 425                 430
Trp Arg Asp Met His His Val Ile Asp Val Leu Tyr Asp Arg Thr Asn
        435                 440                 445
Pro Glu Glu Thr Gln Arg Ala Tyr Ala Cys Phe His Glu Leu Leu Asp
    450                 455                 460
Glu Phe Glu Lys His Gly Tyr Ala Val Tyr Arg Val Asn Thr Ala Phe
465                 470                 475                 480
Gln Glu Arg Val Ala Gln Arg Tyr Gly Thr Val Lys Arg Arg Trp Asn
                485                 490                 495
Thr Pro Ser Ser Ala Pro Trp Thr Arg Thr Thr Ser Trp His Pro Ala
            500                 505                 510
Asn Pro Ala Ser Thr Ser Pro Thr Ser Ser Asn Pro Lys Gln Asp Pro
        515                 520                 525
Ala Gly
    530

<210> SEQ ID NO 7
<211> LENGTH: 20
<212> TYPE: DNA
<213> ORGANISM: Artificial Sequence
<220> FEATURE:
```

```
<223> OTHER INFORMATION: Description of Artificial Sequence:  primer
<220> FEATURE:
<223> OTHER INFORMATION: primer used for sequencing pcu

<400> SEQUENCE: 7
atgaccatga ctcgcaaacc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 8
tttgcgagtc atggtcatgg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 9
cgcgcaaaca agagagaacc                                              20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 10
cattcgatct gcgccttgat gc                                           22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 11
tttgtggtct tggccgatgc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 12
tgacgttgcc gaacacatgg                                              20
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 13
cccagcccca ataaaaaacg g                                           21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 14
gattttctgg tagacgttct cgcc                                        24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 15
cgtctaccag aaaatctgtg g                                           21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 16
atgctgtcgt tctctgcacc                                             20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 17
gacacatcct gaagcagatc c                                           21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu
```

```
<400> SEQUENCE: 18
tgaacactgc gttccaggag c                                     21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 19
ggcagaagag cctgatcgtc g                                     21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 20
actccggaga agtttctgc                                        19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 21
atcagtccgt ggaacttcc                                        19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 22
ttaacgacga gcccaacg                                         18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 23
tgttcggcgt tgtccactgc                                       20

<210> SEQ ID NO 24
<211> LENGTH: 18
<212> TYPE: DNA
<213> ORGANISM: Artificial Sequence
```

```
<220> FEATURE:
<223> OTHER INFORMATION: Description of Artificial Sequence: primer
<220> FEATURE:
<223> OTHER INFORMATION: primer used for sequencing pcu

<400> SEQUENCE: 24
aacttcggtt acggctcg                                                  18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 25
gctcggacta caccactg                                                  18

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 26
atggcaatat ctggctctgc                                                20

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 27
aaaccctcga gcaatccc                                                  18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 28
atgaccaagg ccatgctgg                                                 19

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 29
ttcgctcagg ctgaaacc                                                  18
```

```
<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 30
gtaatggttg gcaatgcgtg g                                           21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 31
tggatggaag tgggctacg                                              19

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 32
ttcgacatcg actccagcat cg                                          22

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 33
agctgctatt gcgcatcg                                               18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu

<400> SEQUENCE: 34
ttggtggcgc tcaactgc                                               18

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:  primer
<220> FEATURE:
<223> OTHER INFORMATION: primer used for sequencing pcu
```

```
<400> SEQUENCE: 35
aaatggccga tctggatgag c                                              21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 36
tatcccactc cactgtccat gg                                             22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 37
caccacttcc atgccgcact gc                                             22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 38
tgcggtaaag ctctccattg g                                              21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 39
caagtaatcg tacagctgct gg                                             22

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 40
agccgtaccc gaagttgcg                                                 19

<210> SEQ ID NO 41
<211> LENGTH: 24
<212> TYPE: DNA
```

```
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 41
tgcgatcatg atcttgttgt aggg                                          24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 42
gatcgagaac gaaacgaatt ggcc                                          24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 43
gtgctgttcg ctcaagctga aacc                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 44
accacaccga tgatgccttg ctgc                                          24

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 45
tatgctggcc gatccactgc acc                                           23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 46
ccttgagcag ggtacgacgt tcg                                           23
```

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 47
atcaccgggc ccacctgttt ttcg                                      24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 48
ttggagatgt actcggcgac ctgc                                      24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 49
tgttgcaggg tgatccagtg atcg                                      24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 50
actccgtttt ttattggggc tggg                                      24

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 51
tggcgatctt ctccttcaaa cc                                        22

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:

<223> OTHER INFORMATION: primer used for sequencing pcu

<400> SEQUENCE: 52
gccgaaaatt tcttcgcg                                                  18

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 53
tggtgcagga acttgcc                                                   17

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 54
gccttgatac gggtgctgc                                                 19

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 55
aagttccacg gactgatcac gcc                                            23

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 56
attcgatctg cgccttgatg cggg                                           24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 57
gtccatgggt tctctcttgt ttgc                                           24

<210> SEQ ID NO 58
<211> LENGTH: 24

```
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 58 ctgtcccttta acaactaacg tgcc                                           24

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 59
gatacgtcag gcaagacg                                                   18

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 60
ctgaatagca ttgttcctac ctcc                                            24

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 61
caccaagctt tgttgatctc ccttcaag                                        28

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 62
ttcggcgcca tccgtcgcga gttggtg                                         27

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 63
```
agcggcatcg gcctgacc                                                 18

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 64
gttgtcaaag aacatgaacc gg                                            22

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 65
tatgtctggc cctctgtgcg gttg                                          24

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 66
agtatgtctc tggccctcgg tg                                            22

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 67
taaacatgcc cagacggtgg                                               20

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 68
gatttgcaga accgtctgtc c                                             21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: primer

```
<220> FEATURE:
<223> OTHER INFORMATION: primer used for sequencing pcu

<400> SEQUENCE: 69
tacggcatgt gcaccaagat ggg                                   23

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 70
aggaattcgg cctgtactac tggc                                  24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 71
agttgctgga tgagttcgag aagc                                  24

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 72
gcatgatgga tcctgcacgt gatatgg                               27

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 73
tgggaacggt acttgaagg                                        19

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 74
gttttcccag tcacgac                                          17

<210> SEQ ID NO 75
```

```
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 75
agcggataac aatttcacac agga                                        24

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing pcu

<400> SEQUENCE: 76
gtaaaacgac ggccagt                                                17

<210> SEQ ID NO 77
<211> LENGTH: 16
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for cloning pcu

<400> SEQUENCE: 77
aacagctatg accatg                                                 16

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for cloning Pseudomonas putida
      (NCIMB 9869) pchC gene

<400> SEQUENCE: 78
gaaattggag ctccaaatga cat                                         23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for cloning a Pseudomonas putida
      (NCIMB 9869) pchC gene

<400> SEQUENCE: 79
ctcatgacag gatcctcaag gct                                         23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX
```

```
<400> SEQUENCE: 80
gttcatacca gtctttacgt ggg                                           23

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 81
ttccatactc tgtacccagc cc                                            22

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 82
attccggtct gcatcaactg c                                             21

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 83
tggtggtatt cggtaccg                                                 18

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 84
tacttccata ctctgtaccc                                               20

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 85
agcaccgaaa cgccagtcat cc                                            22

<210> SEQ ID NO 86
<211> LENGTH: 20
<212> TYPE: DNA
```

```
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 86
gcggacatcc atagagaagc                                              20

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 87
atctctaata ccggtgcc                                                18

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 88
aagcataacc gctcaaaggc                                              20

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 89
attgccccca cgattattgc gacc                                         24

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for sequencing tmoX

<400> SEQUENCE: 90
gattgcccca taaccctcc                                               19

<210> SEQ ID NO 91
<211> LENGTH: 1562
<212> TYPE: DNA
<213> ORGANISM: Pseudomonas mendocina KR-1

<400> SEQUENCE: 91
ggtagttttc ttcaggattt ctctaaacta tcgtttatca acgataaac cttggttcgc    60 ttaattgcga aaattgcata aaccaataat ccaaaaaaca atttatttt atttcgtggt   120 cgcaataatc gtgggtgcaa tcaaacggta ttttcctgct tcactttata agaataagaa  180
```

-continued

```
gaggtagaaa gatgataaaa atgaaaattg ccagcgtact cgtactgcct ttgagcggtt      240
atgcttttag cgtgcacgct acacaggtgt tcgatctgga gggttatggg caatctctc      300 gtgccatggg aggtaccagc tcatcgtatt ataccggcaa tgctgcattg atcagcaacc      360
ccgctacatt gagcttggct ccggacggaa gtcagtttga gctcgggccg atatagtaa      420 gtaccgatat tgaggttcgt gacagcagcg gtgcgaaagt aaaaagcagc acggaatcca      480
ataatcgagg cccctatatc ggtccgcagt tgagctatgt tactcagctg atgactggc      540 gtttcggtgc tgggttgttt gtgagtagtg gctgggtac agagtatgga agtaacagtt      600
tcttgtcaca gacagaaaat ggcacccaaa ccagctttga caattccagc cgtctgattg      660
tgttgcgcgc tcctgtaggc tttagttatc aagtaacacc acaacttaca gtcggcgcaa      720
gtgctgatct ggtctggacc tcactcaatc tcgagcttct actcccatca tctcaggtgg      780
gagcactcgc tgcgcagggt aatctttcag gtgatttagt cgccccactc gctgggtttg      840
tgggtgctgg tggtgctgca catttcagtc taagtcgcaa caacccagtt ggcggtgccg      900
tggatgcaat cgggtggggt gggcgtttgg gtctgaccta caagctcacg ataagacag      960 tccttggtgc gatgtacaac ttcaagactt ctgtgggcga cctcgaaggg acggcaacac     1020
tttctgctat cagcggtgat ggtgcggtgt tgccattaca tggcgatatc cgcgtaaaag     1080
acttcgagat gcccgccagt ctgacgttcg gctttgctca tcaattcaac gagcgttggc     1140
tggttgctgc tgatgtcaag cgtgtctact ggagcgatgt catggaagac atcagtgtgg     1200
atttcaaatc gcagtcaggt gggattgata tcgaattacc acacaactat caggatatta     1260
cggtggcctc catcggcacc gcttacagag ttaatgacaa gctaactctt cgtgctggat     1320
atagctatgc gcaacaggcg ctggacagta ggctgatatt gccagtaatt ccagcttatt     1380
tgaagaaaca cgtttctctc ggtagcgatt atagttttga taaaaaatca aaactcaatt     1440
tggcgatttc ttttggccta aaagagagct tgaacacacc atcataccta gcggcaccg     1500 aaacgttgaa gcaaagccac agccaaataa acgcagtggt ttcctacagc aaaagctttt     1560
aa                                                                    1562
```

<210> SEQ ID NO 92
<211> LENGTH: 456
<212> TYPE: PRT
<213> ORGANISM: Pseudomonas mendocina KR-1

<400> SEQUENCE: 92

```
Met Ile Lys Met Lys Ile Ala Ser Val Leu Val Pro Leu Ser Gly
  1               5                  10                  15

Tyr Ala Phe Ser Val His Ala Thr Gln Val Phe Asp Leu Glu Gly Tyr
                 20                  25                  30

Gly Ala Ile Ser Arg Ala Met Gly Gly Thr Ser Ser Tyr Tyr Thr
             35                  40                  45

Gly Asn Ala Ala Leu Ile Ser Asn Pro Ala Thr Leu Ser Leu Ala Pro
         50                  55                  60

Asp Gly Ser Gln Phe Glu Leu Gly Pro Asp Ile Val Ser Thr Asp Ile
 65                  70                  75                  80

Glu Val Arg Asp Ser Ser Gly Ala Lys Val Lys Ser Ser Thr Glu Ser
                 85                  90                  95

Asn Asn Arg Gly Pro Tyr Ile Gly Pro Gln Leu Ser Tyr Val Thr Gln
            100                 105                 110

Leu Asp Asp Trp Arg Phe Gly Ala Gly Leu Phe Val Ser Ser Gly Leu
```

```
            115                 120                 125
Gly Thr Glu Tyr Gly Ser Asn Ser Phe Leu Ser Gln Thr Glu Asn Gly
            130                 135                 140
Thr Gln Thr Ser Phe Asp Asn Ser Ser Arg Leu Ile Val Leu Arg Ala
145                 150                 155                 160
Pro Val Gly Phe Ser Tyr Gln Val Thr Pro Gln Leu Thr Val Gly Ala
                165                 170                 175
Ser Ala Asp Leu Val Trp Thr Ser Leu Asn Leu Glu Leu Leu Leu Pro
            180                 185                 190
Ser Ser Gln Val Gly Ala Leu Ala Ala Gln Gly Asn Leu Ser Gly Asp
        195                 200                 205
Leu Val Ala Pro Leu Ala Gly Phe Val Gly Ala Gly Ala Ala His
210                 215                 220
Phe Ser Leu Ser Arg Asn Asn Pro Val Gly Ala Val Asp Ala Ile
225                 230                 235                 240
Gly Trp Gly Gly Arg Leu Gly Leu Thr Tyr Lys Leu Thr Asp Lys Thr
                245                 250                 255
Val Leu Gly Ala Met Tyr Asn Phe Lys Thr Ser Val Gly Asp Leu Glu
            260                 265                 270
Gly Thr Ala Thr Leu Ser Ala Ile Ser Gly Asp Gly Ala Val Leu Pro
        275                 280                 285
Leu His Gly Asp Ile Arg Val Lys Asp Phe Glu Met Pro Ala Ser Leu
    290                 295                 300
Thr Phe Gly Phe Ala His Gln Phe Asn Glu Arg Trp Leu Val Ala Ala
305                 310                 315                 320
Asp Val Lys Arg Val Tyr Trp Ser Asp Val Met Glu Asp Ile Ser Val
                325                 330                 335
Asp Phe Lys Ser Gln Ser Gly Gly Ile Asp Ile Glu Leu Pro His Asn
            340                 345                 350
Tyr Gln Asp Ile Thr Val Ala Ser Ile Gly Thr Ala Tyr Arg Val Asn
        355                 360                 365
Asp Lys Leu Thr Leu Arg Ala Gly Tyr Ser Tyr Ala Gln Gln Ala Leu
370                 375                 380
Asp Ser Arg Leu Ile Leu Pro Val Ile Pro Ala Tyr Leu Lys Lys His
385                 390                 395                 400
Val Ser Leu Gly Ser Asp Tyr Ser Phe Asp Lys Lys Ser Lys Leu Asn
                405                 410                 415
Leu Ala Ile Ser Phe Gly Leu Lys Glu Ser Leu Asn Thr Pro Ser Tyr
            420                 425                 430
Leu Ser Gly Thr Glu Thr Leu Lys Gln Ser His Ser Gln Ile Asn Ala
        435                 440                 445
Val Val Ser Tyr Ser Lys Ser Phe
    450                 455

<210> SEQ ID NO 93
<211> LENGTH: 26
<212> TYPE: DNA
<213> ORGANISM: Artificial Sequence
<220> FEATURE:
<223> OTHER INFORMATION: Description of Artificial Sequence:   primer
<220> FEATURE:
<223> OTHER INFORMATION: primer used for cloning pcu for insertion into
      pMC3

<400> SEQUENCE: 93
gatgatgaag cttccccacc aaaccc                                        26
```

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for cloning pcu for insertion into
      pMC3

<400> SEQUENCE: 94
tcatagatca agcttttccc agtcacgacg                                    30

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for construction plasmids pPCUR1
      and pPCUR2

<400> SEQUENCE: 95
ggggatcctc accgccggct caagg                                         25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used for constructing plasmids pPCUR1
      and pPCUR2

<400> SEQUENCE: 96
gcgggtggga tccatgggtt ctctc                                         25

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer used to map the transcript initiation
      site of tmoX

<400> SEQUENCE: 97
cggtacttac tatatccggc ccg                                           23

<210> SEQ ID NO 98
<211> LENGTH: 1836
<212> TYPE: DNA
<213> ORGANISM: Pseudomonas mendocina KR-1

<400> SEQUENCE: 98
tcactccccc ttgagccggt agctgatctg cgcgcgactc atgcccaaca tctgcgccgc    60
cgcggtgagg ttgccgccgg tgcgttccag ggcaaggtgc accaggcgct gctcgatctc   120
cttcagtgat gtgcctagta cccggtcgcg cccggcgagg aaggcctgca ggttggccag   180
ccccagctca accggttcat gctcctcgac aaccacctca gcccgcgctt gcggttcgcc   240
gccgacggca tccagacggc cttcggcggt caggccgatg ccgctggagc gaagtggctc   300

| | |
|---|---|
| gccggctttt gccaggtgca ccaggtcgat cagctcgcca ctgcctgcgg cgatcacgcc | 360 |
| gcgctcgatc aggttctgca gctcacggat attgccgggg aagcgtagg tcagcagcgc | 420 |
| gttgaccagc cgcgtgctga aacccagggg tttgagccca tggcgcgcac tgaacttgcg | 480 |
| caggaagtag ctcatcagga gcgggatgtc ctcacgcgcg tcgcgcaggg gcggcagatg | 540 |
| gatgggaac acgttcagcc ggtacagcag gtcctcgcgg aagcgcccgg cctcgacctc | 600 |
| tcggcgcagg tccagattgg tggcggcgat caccctcaca tccaccggga tcgccgaggt | 660 |
| accacctacc cgctcgatct cgccctcctg cagcacccgc aggatcttgc tctgggcgct | 720 |
| gaggctcagg gtggcgatct cgtcgaggaa cagggtgccg ccttggccc gctcgaagcg | 780 |
| ccccgggcgg gaacggtcgg cgccggtgaa ggcaccgcgc tccacgccga acagttcggc | 840 |
| ttccagcaga gtttccggca acgccgcgca gttgagcgcc accaacggcg tttggcggcg | 900 |
| cgggctggcc tggtgcaggg tgcgcgcgaa gagctccttg cccaccccg attcaccggt | 960 |
| cagcagtacg gtggcctggg tcgacgcaac gcggtagagc tgctggctgg cggcgacaaa | 1020 |
| ggcggcggaa atgcccacca tggcctggtc ctcgggcggc tcatccagat cggccatttc | 1080 |
| cgtctcgtct gccgagccgt aggtgctccg gctgaggaag tcgctggcat ccaggtgggc | 1140 |
| caggtcggtg tcgatgtcct cccactgctc cgccggcttg ccgacgatgc ggcacgccga | 1200 |
| atggcccatg cagcggcatt cctgctcgcg gaacaccacc aggcgcccca gcagggagga | 1260 |
| ggtgtagccg ctggcgtagc ccacttccat ccagcaggcc ggttcgctgc ccagcccgta | 1320 |
| gctggcgatg tgctcgtcgg cttccaggga gttgtgccag aagaattcgg aatagaaatg | 1380 |
| cccgatgctg gagtcgatgt cgaagcgcac cacttccacg ttcaccatgc cctccagcat | 1440 |
| gtgcaggcgc gggcctgcgc tgtagaggct ggcgtggtcg ccctcgggcc actgcgcgct | 1500 |
| gacctgagcg gcatccctcg ttccggcctg ccagccaatg cgggtcagaa ggccacgggc | 1560 |
| cttgtcgagg ccgagggctt ccaccaactc gcgacggatg gcgccgaagg cggccccctg | 1620 |
| cagcagcatc atgcgctggc cgcagagcca gatattgcca tcctggggcg cgaaggcgac | 1680 |
| ggtctccgcc agttgctcgg ccgagggcag cccgctgctg ccgaactggt tggcctggtc | 1740 |
| gacgatcagg ctcttctgcc ggccgagcaa ctgcttgagg aattcatccc ccatgctgcg | 1800 |
| gccgggattg ctcgagggtt tgcgagtcat ggtcat | 1836 |

<210> SEQ ID NO 99
<211> LENGTH: 1476
<212> TYPE: DNA
<213> ORGANISM: Pseudomonas mendocina KR-1

<400> SEQUENCE: 99

| | |
|---|---|
| atggacacca cccgccctgc ctaccagaac ctcgagctcc aacctctcgc cgggcaatgg | 60 |
| cgcgccggca gtagcggtcg cccgttggag gtcttcgacc cctacaacga cgagctgcta | 120 |
| ttgcgcatcg ccctggccag ccgcgaagac ctcgacgcag cctaccgcaa ggcccgcgac | 180 |
| agccagcggg agtgggcgac cacggcgccg gccgagcgcg cccgggtgct gctggaagcg | 240 |
| gtgaagatct tcgatgagcg ccgcgaggag attatcgact ggatcatccg cgagtccggc | 300 |
| agcacccgca tcaaggcgca gatcgaatgg ggcgccgccc gcgccatcac cctggagtcg | 360 |
| gccagcctgc cgaatcgcgt gcacgggcgc atcatcgcct ccaacatctc cggcaaggag | 420 |
| agccgcgtgt accgcgcgcc cctgggcgtg atcggcgtga tcagtccgtg gaacttcccc | 480 |
| ctgcacctca ctgcccgctc cctggcccg gcctggcc tgggcaatgc cgtggtggtc | 540 |
| aagccggcca gcgacacccc gatcaccggt ggcctactgc tggcgcgcat cttcgaagaa | 600 |

-continued

```
gccggcctgc cggcgggcgt gctcagcgtg gtggtgggtt cgggcgcgga gattggtgac    660
gccttcgtcg agcacccggt gcccgccctc atttccttca ccggctccac tcaggtgggc    720
cgcaacatcg gccgcatcgc cagcggcggt gagcacctca gcacgtggc gctggaactg    780 ggcggcaaca gcccgtttgt ggtcttggcc gatgccgacg tggagcaggc ggtgaatgcg    840
gccgtggtcg gcaagttcct gcaccagggc cagatctgca tggcgatcaa ccgcattatc    900
gtcgagcagc ctttgctgga agatttcacc cgccgcttcg tcgagcgcgt caaggccctg    960
ccctatggcg acccgagcaa gccggggacc gtggtcggtc cggtgatcaa cgccaggcag   1020
ctggccggtc tgaaggagaa gatcgccacc gccaaggccg aaggcgccac cctgctgctg   1080
ggtggcgagc cccagggcaa cgtcatgccg ccccatgtgt tcggcaacgt caccgccgac   1140
atggaaatcg cccgcgaaga aattttcggc cgctggtgg gcatccaatc cgcccgtgac   1200
gccgaacacg ccctggagtt ggccaacagc agcgagtacg gcctgtccag cgcggtgttc   1260
accgccagcc tcgagcgcgg cgtgcagttc gcccggcgca tccacgccgg catgacccac   1320
gtgaacgaca tcccggttaa cgacgagccc aacgctccct tcggcggcga gaagaactct   1380
ggcctcggcc gcttcaacgg cgactgggcc atcgaggagt tcaccaccga tcactggatc   1440
accctgcaac acagcccgcg gccctatccg ttctga                              1476
```

<210> SEQ ID NO 100
<211> LENGTH: 336
<212> TYPE: DNA
<213> ORGANISM: Pseudomonas mendocina KR-1

<400> SEQUENCE: 100

```
atgtcctcac tcctcaacag ccgagctgtg aaacggccac tgctggccag ccttgcacta    60
attttcgccc tgctcgccgg ccaggccttc gccgacggcg acggcgtctg gaaaggcggc   120
gagaacgtct accagaaaat ctgtggccac tgccacgaaa acaggtgggg cccggtgatc   180
accggccgcc agctaccgcc gcagtacatc agtgccgtgg tgcgcaacgg cttccgcgcc   240
atgccggcct tccggcctc gttcatcgac gacaaggccc tgcagcaggt cgccgagtac   300
atctccaaga cccctgctac tgtggccaag ccctga                              336
```

<210> SEQ ID NO 101
<211> LENGTH: 684
<212> TYPE: DNA
<213> ORGANISM: Pseudomonas mendocina KR-1

<400> SEQUENCE: 101

```
atgaacatcg aacgtcgtac cctgctcaag ggcatggccc tgggcggcct ggctggcgcc    60
gccatgggcg ccttcggcct ggcgatgacc aaggccatgc tgggcgggca ggcccagcca   120
ctgcccaccc tcgtcctggt agatggcgag gcggccggag cggccttcct cgccggagtc   180
ggttccagcc cggcggccag caaggccgag gtgcagcgca ccgatctcgg cctggacttc   240
gtcttgggcc tggagaagcg cctgcgcagt ggtcagcagc aacgcatcat cggtctggtg   300
gatgacgcca gcgccgctct gatcctcgac ctggcccgca gcaggcgcgc gcgggtgcag   360
tggctcggcc agcatagcgc cgcggccggc tcctcccggc accgtctgct cagcgccgac   420
agcgcccagg gctgctccct tcgcctgggc cagcagctcc atgcctgcgg cggcggcttc   480
agcctgagcg aacagcaccc cctggtggc cagcccctga atctggccgg tgccgcgcgc   540
agcggcggct ccgcgcaatg ggcggccagc atcggccacg acctggccag cctgggcggc   600
```

| gatgacagca | gtgcggcccc | acgcattgcc | aaccattacc | cggcgcttac | cggccaattc | 660 |
| gtttcgttct | cgatcctggt | ttga | | | | 684 |

<210> SEQ ID NO 102
<211> LENGTH: 1593
<212> TYPE: DNA
<213> ORGANISM: Pseudomonas mendocina KR-1

<400> SEQUENCE: 102

| atgaccgagc | aaacccagaa | caccctgatt | ccccgtggcg | tgaatgacgc | caacctccag | 60 |
| caagccctgg | ccaagttccg | caagctgctg | ggcgaggaca | acgtcctggt | caaggacgag | 120 |
| caactcatcc | cctacaacaa | gatcatgatc | gcagtggaca | acgccgaaca | cgcgccctcc | 180 |
| gctgctgtca | ccgccaccac | tgtggaacag | gtgcagggcg | tggtgaagat | ctgcaacgaa | 240 |
| tacggcattc | cggtgtggac | catctccacc | ggccgcaact | tcggttacgg | ctcggcggcc | 300 |
| cccgccagc | gtggccaggt | gatcctcgac | ctgaagaaaa | tgaacaagat | catccacgta | 360 |
| gacccggacc | tgtgcaccgc | cctggtggaa | cgggggtga | cctaccagca | gctgtacgat | 420 |
| tacctggaag | agaacaacat | cccgctgatg | ctgtccttct | ctgcaccctc | ggccatcgcc | 480 |
| ggcccgctgg | gcaacaccat | ggaccgtggc | gtgggctaca | cccctacgg | cgagcacttc | 540 |
| ctcatgcagt | gcggcatgga | agtggtgctg | gccaatggcg | acgtctaccg | caccggcatg | 600 |
| ggcggggtga | aggcgacaa | cgcctggcag | gtgttcaagt | ggggctacgg | cccgaccctg | 660 |
| gacggcatgt | tcacccaggc | caactacggc | atctgcacca | agatgggttt | ctggctgatg | 720 |
| cccaagcccc | cggtgttcaa | gcccttcgag | atcaagttcg | agaacgagtc | cgacatcagc | 780 |
| gagatcgtcg | aattcatccg | tccgctcgc | atcgcccagg | tcatcccaaa | ctccgtggtg | 840 |
| atcgccggtg | tgctctggga | ggcctccacc | tgcaataccc | gccgtcgga | ctacaccact | 900 |
| gagccgggcg | ccactcccga | caccatcctg | aagcagatcc | agaaggacaa | ggaactcggc | 960 |
| gcctggaacg | tctatgccgc | tctctacggc | acgcaggaac | aggtggacgt | gaactggaag | 1020 |
| atcgtcaccg | cgcccctggc | caaactgggc | aagggcagga | ttgtcaccca | ggaagaggcc | 1080 |
| ggcgataccc | agcccttcaa | gtaccgttcc | cagttgatgt | ccggcgtccc | caacctgcag | 1140 |
| gaattcggcc | tgtacaactg | cgcgggggc | ggcggctcca | tgtggttcgc | cccggtcagc | 1200 |
| caggcccgtg | gcatcgagtg | cgacaagcag | caggcgctgg | ccaagaagat | cctcaacaag | 1260 |
| cacgccctgg | actacgtcgg | cgagttcatt | gtcggctggc | gcgacatgca | ccacgtaatc | 1320 |
| gacgtgctgt | acgaccgcac | caaccccgag | gaaacccaac | gcgcctacgc | ctgcttccac | 1380 |
| gagttgctgg | atgagttcga | gaagcacggc | tatgcggtgt | accgcgtgaa | cactgcgttc | 1440 |
| caggagcgcg | tggcgcagag | gtacggcacg | gtcaagcgca | ggtggaacac | gccatcaagc | 1500 |
| gcgccctgga | cccgaacaac | atcctggcac | ccggcaaatc | cggcatcgac | ctcgccaaca | 1560 |
| agttctaacc | ctaagcaaga | ccccgccggg | taa | | | 1593 |

<210> SEQ ID NO 103
<211> LENGTH: 1371
<212> TYPE: DNA
<213> ORGANISM: Pseudomonas mendocina KR-1

<400> SEQUENCE: 103

| atgataaaaa | tgaaaattgc | cagcgtactc | gtactgcctt | tgagcggtta | tgcttttagc | 60 |
| gtgcacgcta | cacaggtgtt | cgatctggag | ggttatgggg | caatctctcg | tgccatggga | 120 |
| ggtaccagct | catcgtatta | taccggcaat | gctgcattga | tcagcaaccc | cgctacattg | 180 |

```
agcttggctc cggacggaag tcagtttgag ctcgggccgg atatagtaag taccgatatt    240
gaggttcgtg acagcagcgg tgcgaaagta aaaagcagca cggaatccaa taatcgaggc    300
ccctatatcg gtccgcagtt gagctatgtt actcagctgg atgactggcg tttcggtgct    360
gggttgtttg tgagtagtgg gctgggtaca gagtatggaa gtaacagttt cttgtcacag    420
acagaaaatg gcacccaaac cagctttgac aattccagcc gtctgattgt gttgcgcgct    480
cctgtaggct ttagttatca agtaacacca caacttacag tcggcgcaag tgctgatctg    540
gtctggacct cactcaatct cgagcttcta ctcccatcat ctcaggtggg agcactcgct    600
gcgcagggta atctttcagg tgatttagtc gccccactcg ctgggtttgt gggtgctggt    660
ggtgctgcac atttcagtct aagtcgcaac aacccagttg gcggtgccgt ggatgcaatc    720
gggtggggtg ggcgtttggg tctgacctac aagctcacgg ataagacagt ccttggtgcg    780
atgtacaact tcaagacttc tgtgggcgac ctcgaaggga cggcaacact ttctgctatc    840
agcggtgatg gtgcggtgtt gccattacat ggcgatatcc gcgtaaaaga cttcgagatg    900
cccgccagtc tgacgttcgg cttttgctcat caattcaacg agcgttggct ggttgctgct    960
gatgtcaagc gtgtctactg gagcgatgtc atggaagaca tcagtgtgga tttcaaatcg    1020
cagtcaggtg ggattgatat cgaattacca cacaactatc aggatattac ggtggcctcc    1080
atcggcaccg cttacagagt taatgacaag ctaactcttc gtgctggata tagctatgcg    1140
caacaggcgc tggacagtag gctgatattg ccagtaattc cagcttattt gaagaaacac    1200
gtttctctcg gtagcgatta tagttttgat aaaaaatcaa aactcaattt ggcgatttct    1260
tttggcctaa aagagagctt gaacacacca tcatacctaa gcggcaccga aacgttgaag    1320
caaagccaca gccaaataaa cgcagtggtt tcctacagca aaagctttta a            1371
```

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 104
gcttccacgg tatctcg                                                   17

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 105
cagtcaatcc gctgcac                                                   17

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

```
<400> SEQUENCE: 106
gcagtatggt cacctgttcc                                          20

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 107
ggttcgacca ccaggctac                                           19

<210> SEQ ID NO 108
<211> LENGTH: 19
<212> TYPE: DNA
<213> ORGANISM: Artificial Sequence
<220> FEATURE:
<223> OTHER INFORMATION: primer

<400> SEQUENCE: 108
ggatctcaaa gccctgacc                                           19

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 109
tgctgcacaa ggccggtatc g                                        21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 110
ggtcatgaac cagctgaagc g                                        21

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 111
cctgtccgtt aatcgaacg                                           19

<210> SEQ ID NO 112
<211> LENGTH: 3554
<212> TYPE: DNA
<213> ORGANISM: Pseudomonas putida

<400> SEQUENCE: 112
```

```
atgagctcct tggatagaaa aaagcctcaa aatagatcga aaaataatta ttataatatc    60
tgcctcaagg agaaaggatc tgaagagctg acgtgtgaag aacatgcacg catcatattt   120
gatgggctct acgagtttgt gggccttctt gatgctcatg gaaatgtgct tgaagtgaac   180
caggtcgcat tggagggggg cgggattact ctggaagaaa tacgagggaa gccattctgg   240
aaggcgcgtt ggtggcaaat ttcaaaaaaa accgaggcga cccaaaagcg acttgttgaa   300
actgcatcat ccggtgaatt tgttcgctgt gatgttgaga ttcttggaaa atcaggtgga   360
agagaggtaa tatcggtcga tttttcattg ctgccaattt gcaatgaaga agggagcatt   420
gtttaccttc ttgcggaagg gcgcaatatt accgataaga agaaagccga ggccatgctg   480
gcgttgaaga accaggaatt ggagcagtcg gttgagtgta ccgaaaaact cgataatgcg   540
aagagtgatt tctttgccaa ggtgagccat gagttgcgca ctccgctgtc tttgattcta   600
ggccactgga agccgttatg gcgggcagag gctgggcgtg aatcgccgta ttggaagcag   660
tttgaggtca ttcagcgtaa tgcaatgacc ctgttgaaac aggttaacac gctgcttgac   720
ttggcgaaaa tggacgcccg gcagatgggg cttttcctat cggcgagcca atcttagtcag   780
ctcacccgta ctattagctc gaattttgaa ggaatagccc agcaaaaatc aataacgttc   840
gatacaaaac tgcctgtaca gatggtcgct gaggtggatt gtgagaaata cgaacgcatt   900
atccttaact tgctttccaa tgcgtttaaa ttcacccctg acgggggggct tatccgttgc   960
tgtcttagtt tgagtcgacc aaattatgcc ttggttactg tatctgatag cgggccgggt  1020
attcctcctg cactgcgtaa agaaatattt gaacgtttcc accagctaag ccaggaaggt  1080
caacaagcta cgcggggtac aggcttgggg ctttccattg tgaaagaatt cgttgaattg  1140
caccgtggaa caatttctgt aagtgatgcc ccgggcgggg gggcgctttt tcaggtaaag  1200
ctgccgctga atgctcctga aggtgcttat gttgcgagta acaccgcgcc gcgaagagat  1260
aatcctcagg tcgtggatac ggatgagtac cttttgctgg cgcccaatgc ggaaaatgaa  1320
gccgaggtgc ttccatttca atccgaccag cctcgggtgc taatcgttga agataaccct  1380
gatatgcgtg gttttataaa ggactgtctc agtagcgact atcaagttta tgttgcaccc  1440
gacggtgcaa aggcattgga gttgatgtca acatgccgc cagacctgtt gattacagac  1500
ctgatgatgc tgttatgag cggcgatatg ctggttcacc aagtgcgtaa gaaaaatgaa  1560
cttttcacata tcccgatcat ggtgctgtcg gccaagtcag acgcagaact gcgtgtgaaa  1620
ttgctctccg agtcggtgca ggactttctt cttaagccat tttctgctca tgagctacga  1680
gcgcgtgtaa gcaatctggt atccatgaag gtggcaggcg atgcgttgcg taaggagctt  1740
tccgatcagg gggatgatat tgcgatactt actcaccgtc tgatcaaaag tcgccatcgt  1800
cttcagcaga gtaacatcgc attatccgcc tcggaagcgc gttggaaagc agtgtatgaa  1860
aactctgcgg ccggtattgt actgaccgac ccggaaaacc gaatactcaa cgccaatcct  1920
gcatttcaac gcattaccgg atatggggaa aaggatttgg agggactttc catggagcaa  1980
ttgactccat ctgacgaaag cccacagata agcagcgtc tggccaattt gcttcagggt  2040
gggggagcgg aatacagtgt ggagcgctcc tatctatgca aaaatggttc tacgatttgg  2100
gccaatgcga gtgtctcgct gatgcctcaa cgtgtcggtg aatctccagt tatactgcag  2160
atcatcgatg acatcactga aagaaacaa gcacaggaaa atcttaacca attgcagcaa  2220
caacttgtgt acgtttcccg atcagctacg atgggtgaat ttgcagccta tattgcacac  2280
gagataaacc aaccgctctc ggcgatcatg accaatgcca atgctggcac acgttggtta  2340
```

-continued

```
ggtaatgagc catctaacat cccagaggct aaagaggcac tggctcgcat tatccgagat    2400
tccgaccgcg ctgcagaaat tatccgtatg gtacgctcct tcctgaagcg tcaagaaacg    2460
gtgctgaaac cgattgatct aaaagcactg gtaactgata caagcctgat acttaaggcc    2520
cctagtcaga ataacagtgt caatttggat gttgttgcgg atgatgaact ccctgagata    2580
tggggggatg gtgtacagat ccagcagttg ataataaatc tggctatgaa cgctattgaa    2640
gcgatcagcc aagccgactg tgaaaccagg cagctaaccc tgtcattctc aggcaatgat    2700
acaggtgatg cgcttgttat ctcagtgaaa gatacaggtc caggtatttc agagaggcag    2760
atggcgcagt tgttcaacgc attctacacc acaaaaaaag aagggcttgg tatgggattg    2820
gcaatctgtc ttacaatcac ggaagtgcat aacggtaaaa tatgggttga gtgcccgccc    2880
gctgggggtg cttgtttcct ggtaagtatc cctgccagac agggctccgg cacatgagtg    2940
atcgggcatc tgttatctat atcctcgatg acgacaatgc agtactggaa gcactgagca    3000
gcttggtgcg ttcaatcggc ctgagtgtcg agtgttttc atccgctagc gtattcctga    3060
acgatgtcaa tcgctctgcc tgtggctgtc taattttgga tgtccgtatg cccgagatga    3120
gcgggttgga tgtgcaacga caactgaaag agcttggcga gcaaatcccc attattttta    3180
tcagcggcca cggtgatatt ccgatggcag tcaaagcgat caaggcgggt gcggtagact    3240
tcttcactaa acctttcga gaagaggagc tgcttggcgc tattcgcgcc gcgctgaagt     3300
tggcgcccca gcagagatca aacgctcccc gagtcagcga gcttaaagag aattacgaaa    3360
gcctcagcaa acgcgagcaa caggtgctta agttcgtctt gcgaggatat ctaaacaagc    3420
agacggctct agagcttgat atatcggaag caacagtgaa agtgcaccgc cataatatca    3480
tgaggaaaat gaaagtatct tcaatccagg atctggttcg agtaactgag cggctcaagg    3540
atagcctgga atag                                                     3554
```